United States Patent
Kawahara et al.

(10) Patent No.: US 6,562,371 B1
(45) Date of Patent: May 13, 2003

(54) LIPOSOMES

(75) Inventors: Kazuo Kawahara, Kanagawa (JP);
Hideto Ushijima, Kanagawa (JP);
Hideki Uchiyama, Kanagawa (JP);
Junji Kimura, Kanagawa (JP)

(73) Assignee: Terumo Kabushiki Kaisha, Tokyo (JP)

(*) Notice: Subject to any disclaimer, the term of this patent is extended or adjusted under 35 U.S.C. 154(b) by 0 days.

(21) Appl. No.: 09/582,710

(22) PCT Filed: Nov. 2, 1999

(86) PCT No.: PCT/JP99/06108

§ 371 (c)(1),
(2), (4) Date: Sep. 21, 2000

(87) PCT Pub. No.: WO00/25748

PCT Pub. Date: May 11, 2000

(30) Foreign Application Priority Data

Nov. 2, 1998 (JP) ............................................. 10-311620
Jun. 10, 1999 (JP) ............................................. 11-163595

(51) Int. Cl.[7] ............................................. A61K 9/127
(52) U.S. Cl. ................. 424/450; 424/1.21; 424/9.321; 424/9.51; 428/402.2
(58) Field of Search ................. 424/450, 1.21, 424/9.321, 9.51; 428/402.2

(56) References Cited

FOREIGN PATENT DOCUMENTS

| EP | 0636363 A2 | 1/1995 |
|---|---|---|
| JP | 7-89874 | 4/1995 |
| JP | 08-027030 | 1/1996 |
| JP | 10-506622 | 6/1998 |
| WO | 96/10391 | 4/1996 |

OTHER PUBLICATIONS

C. Miller et al., *Biochemistry*, 37:12875–12883 (1998).

*Primary Examiner*—Gollamudi S. Kishore
(74) *Attorney, Agent, or Firm*—Burns, Doane, Swecker & Mathis, LLP

(57) ABSTRACT

This invention provides a liposome having a drug included therein, which has active targeting property and ensured stability in blood and can be used effectively in the diagnosis and/or treatment of diseases, particularly renal diseases, that accompany production of proteoglycan, comprising (1) a basic compound which takes positive charge within a physiological pH range, (2) a lipid derivative of a hydrophilic polymer and (3) a lipid which constitutes the liposome, as its membrane constituting components, wherein their constituting ratios are from 1 to 20 mol % of (1) based on (3) and from 0.2 to 5 mol % of (2) based on the total of (1) and (3).

14 Claims, 8 Drawing Sheets

LIPOSOMES

This application is a 371 of PCT/JP99/06108 filed Nov. 2, 1999.

TECHNICAL FIELD

This invention relates to a liposome having active targeting property and ensured stability in blood, which can be used in the diagnosis and/or treatment of diseases, particularly renal diseases, that accompany production of various types of proteoglycan in injured portions of tissues and/or organs.

BACKGROUND ART

In recent years, there have been increased studies on a drug delivery system (DDS) based on a so-called targeting technique in which a drug is efficiently distributed in an organ of interest. Liposomes are one of the most extensively studied means as such a DDS because of their ability to include, or trap, drugs therein.

However, there are various problems to be resolved in putting these liposomes into practical use, particularly, the difficulties in escaping from the mechanism of living body for recognizing foreign bodies and in controlling intracorporeal kinetics. That is, liposomes cause aggregation in blood by their mutual reaction with various blood plasma proteins, including opsonin, and are captured by a reticuloendothelial system (RES) such as in the liver or spleen, so that it has been difficult to deliver liposomes selectively to the target tissues or cells.

In recent years, it became possible to prevent aggregation of liposomes in blood and avoid being captured by RES, by coating the surface of liposome with a hydrophilic polymer such as polyethylene glycol (PEG) and thereby preventing adsorption of various blood plasma proteins, including opsonin, to the liposome surface (U.S. Pat. No. 5,013,556, U.S. Pat. No. 5,676,971).

There are a number of studies based on these techniques with regard to the targeting at tissues of interest, such as tumor tissues, regions of enhanced vascular permeability, inflamed tissues, the liver, the brain and lymph tissues, but all of these cases are based on the effect of so-called passive targeting property, which is induced as a result of the improvement of the stability in blood by avoiding the capture by RES (*Advanced Drug Delivery Reviews*, 24 (1997), 337–334), so that concern has been directed toward the development of a liposome having the ability to bind to the tissues of interest, in which the targeting function is reinforced by so-called active targeting techniques.

Regarding the active targeting techniques, methods for the modification of the liposome surface with target factors such as antibodies, antibody fragments, amino acids, peptides or saccharides have been studied, as well as techniques for making the liposome surface into cationic nature. Particularly, the cation formation can be cited as one of the desirable modification techniques, because it has the ability to deliver genes and the like into cells, as a gene introducing technique, and it improves accumulation of liposome on, for example, an injured portion of vascular endothelium (JP-A-7-89874; the term "JP-A" as used herein means an "unexamined published Japanese patent application"). However, strong aggregation and the like phenomena mediated by the binding of blood protein to liposome were observed by the cationic liposome when compared with a neutral or anionic liposome (*Biochimica et Biophysica Acta*, 1280 (1996), 149–154), so that its sufficient active targeting property in the living body was not obtained as such.

On the other hand, proteoglycans which keep the cell surface anionic are known as the components which their interactions to cationic liposome are expected. It has been reported that overproduction of various types of proteoglycans occurs in tissues of fibrosis in a large number of organs (the liver, the lungs, the heart, the pancreas, the bone marrow and arteries) of tumors such as large bowel cancer, of cell proliferative nephritis and of other inflammatory diseases (*Acta Pathol. Jpn.*, 36 (6): 827 (1986), *FEBS Lett.*, 244: 315 (1988), *J. Rheumatol.*, 18 (10): 1466, (1991), *J. Dent. Res.*, 71 (9): 1587, (1992). This reaction in the living body is considered to be a result of excess repairing reaction which occurs during the step of wound healing or of excess cell proliferation in a tumor or the like tissue, so that it is used as a pathological marker of the foci of the aforementioned diseases.

However, very little is known about reports which aim at achieving active targeting for tissues and/or organs in which such proteoglycan is overproduced. For example, JP-A-8-27030 describes that a drug carrier whose surface is modified with a basic compound which takes positive charge within a physiological pH range is accumulated on a cortical portion of the kidney, but there are no reports which disclose a targeting technique for the specific accumulation of a carrier on renal glomerulus, particularly renal glomerulus which caused inflammation by an injury, and proteoglycan producing tissues and/or organs typified thereby.

Glomerulonephritis is one of the diseases so far reported in which production of various types of proteoglycan is accelerated in injured portions (*Clin. Exp. Immunol.*, 108: 69, (1997), *Kidney International*, 49: supple. 54, s 55 (1996), *J. Am. Soc. Nephrol.*, 2: s 88 (1992)). Importance of the targeting of a drug for a tissue and/or organ overproducing proteoglycan can easily be understood by merely citing this case of glomerulonephritis.

According to the materials produced in 1996 by The Japanese Society of Dialysis Medicine, it is said that about 27,000 patients are subjected to dialysis due to renal insufficiency, and about 50% of the cases is caused by chronic nephropathy, and about 30% thereof by diabetic nephropathy. Since the primary disease in both of the chronic nephropathy and diabetic nephropathy is glomerulonephritis, these patients will be released from the struggling against dialysis when an effective method for the treatment of glomerulonephritis is established. Up to now, however, no effective glomerulonephritis treating method has been found.

For example, a glomerulonephritis, called IgA nephritis, is a glomerulonephritis most frequently found in the Japanese people, and it is said that its patients are estimated to be close to 300,000 in Japan alone and it occupies around 40% of the glomerulonephritis in adults and close to 30% of that in children. As a result of a follow up study carried out in Japan for recent 20 years, it was found that about 40% of IgA nephritis cases, estimated to be 5,000 to 6,000 cases per year (1995), reached terminal renal insufficiency and were subjected to dialysis, so that it is considered that the development of a therapeutic method specific for IgA nephritis is a world-wide pressing need. However, close to 5,000 patients have been subjected to dialysis every year because of the absence of sufficient means for its treatment.

It has been reported that, as a result of 10 years of clinical efficacy evaluation on IgA nephritis, the steroid therapy which is now actively used in Japan for nephrotic syndrome and rapidly progressive glomerulonephritis, and its efficacy is said to be established, also has a possibility of keeping renal functions for a prolonged period of time by its 2 to 3 years of continuous use at an early stage of progressive IgA nephritis.

On the other hand, however, side effects become a serious problem when it is continuously administered for a certain period for such a chronic disease, because problems such as arteriosclerosis, osteoporosis and immunity reduction in adults, slow development in children and the like cannot be avoided. As a result, it becomes a problem that its sufficient efficacy cannot be obtained, because not only QOL (quality of life) of the patient is reduced but also its administration cannot be continued due to side effects and, particularly, its administration for a prolonged period of time is impossible.

In order to resolve these problems, it is necessary to think out a means for expressing its drug effect alone, by a dose which does not express the aforementioned side effects, and it is desirable for this purpose to design a system for efficiently delivering a drug to the glomerulus which caused inflammation by an injury.

The same requirement is also applied to other diseases in which proteoglycan is excessively produced in injured portions of tissues and/or organs, so that it is expected to develop a method which can exert sufficient therapeutic effect without inducing side effects, by actively targeting the organ of interest with a drug which shows a strong drug effect but cannot be used due to its toxicity.

In consequence, this problem is resolved by including a drug into a liposome which is efficiently accumulated on tissues and/or organs that accompany production of proteoglycan, typified by renal glomerulus which caused inflammation by an injury, and by delivering the drug efficiently to such tissues and allowing it to perform continuous action. This purpose is achieved by realizing a liposome having active targeting property and ensured stability in blood, which also has the ability to be accumulated on injured portions of tissues and/or organs that accompany production of various types of proteoglycan.

DISCLOSURE OF THE INVENTION

Accordingly, this invention contemplates providing a liposome having active targeting property and ensured stability in blood, which can be used in the diagnosis and/or treatment of diseases, particularly renal diseases, that accompany production of various types of proteoglycan in injured portions of tissues and/or organs.

In the process of carrying out studies on factors which control intracorporeal kinetics of liposome, the present inventors have found surprisingly that, when a liposome is prepared by incorporating a basic compound which takes positive charge within a physiological pH range, within a certain range of mixing ratio, and combining a hydrophilic polymer to its surface in an amount controlled within a certain range, it shows such properties that not only its stability in blood is ensured, its capture by the liver and the like can be avoided and its retention in blood is improved, but also its ability to recognize proteoglycan in injured portions is sharply improved.

It was found also that, when its major particle size range is from 90 to 200 nm, its accumulation on and selectivity and persistency of the effects are improved for tissues and/or organs in the living body, where proteoglycan is produced in excess amount, particularly for renal glomeruli. In this case, the term "major particle size range" means a range of particle size in which 70% or more of particles are included when the particle size distribution of liposomes is defined by scattering intensity distribution in the particle size measurement based on the laser light scattering methods.

The present inventors have accomplished this invention by conducting intensive studies based on the aforementioned new knowledge.

Accordingly, the present invention provides a liposome in which a drug is included, which comprises (1) a basic compound which takes positive charge within a physiological pH range, (2) a lipid derivative of a hydrophilic polymer and (3) a lipid which constitutes the liposome, as its membrane constituting components, wherein their constituting ratios are from 1 to 20 mol % of (1) based on (3) and from 0.2 to 5 mol % of (2) based on the total of (1) and (3).

More preferred is a liposome which comprises (1) a basic compound which takes positive charge within a physiological pH range, (2) a lipid derivative of a hydrophilic polymer and (3) a lipid which constitutes the liposome, as its membrane constituting components, wherein their constituting ratios are from 5 to 15 mol % of (1) based on (3) and from 0.2 to 5 mol % of (2) based on the total of (1) and (3).

The aforementioned basic compound which takes positive charge within a physiological pH range is preferably a basic compound which has an amidino group, a basic compound which has two or more amino groups, a basic compound which has a piperidine ring or a basic compound which has a quaternary amine, more preferably any one of those represented by the following formulae 1 to 4.

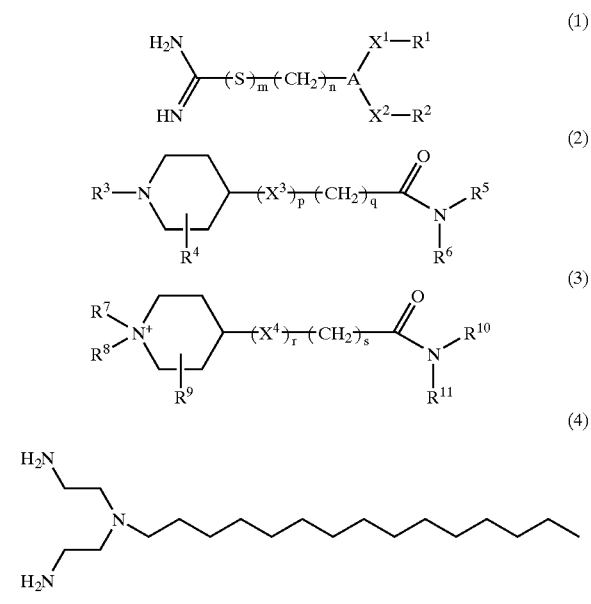

In this connection, the compound of formula 1 is described in WO 97/42166, the compounds of formulae 2 and 3 are described in JP-A-9-263579 and the compound of formula 4 is described in *Chem. Papers*, 39 (1), 125–134 (1985), but these documents describe nothing about a liposome having active targeting property and ensured safety in blood, which can be used in the diagnosis and/or treatment of diseases, particularly renal diseases, that accompany production of various types of proteoglycan in injured portions of tissues and/or organs.

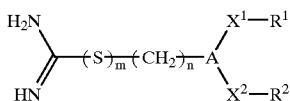

(1)

(In the formula 1, A represents an aromatic ring, each of $R^1$ and $R^2$ represents an alkyl or alkenyl group having from 10 to 25 carbon atoms, wherein $R^1$ and $R^2$ may be the same or different from each other, each of $X^1$ and $X^2$ represents —O—, —S—, —COO—, —OCO—, —CONH— or —NHCO—, wherein $X^1$ and $x^2$ may be the same or different from each other, m is 0 or 1 and n is 0 or an integer of from 1 to 6.)

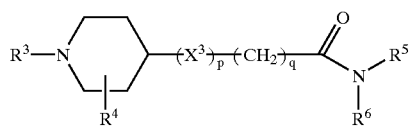

(2)

(In the formula 2, $R^3$ represents hydrogen or an alkyl or alkenyl group having from 1 to 8 carbon atoms, $R^4$ represents hydrogen or an alkyl or alkenyl group having from 1 to 8 carbon atoms, each of $R^5$ and $R^6$ represents hydrogen or an alkyl or alkenyl group having from 1 to 25 carbon atoms (excluding a case in which $R^5$ and $R^6$ are both hydrogen), wherein $R^5$ and $R^6$ may be the same or different from each other, $X^3$ represents —O— or —S—, p is 0 or 1 and q is 0 or an integer of from 1 to 10.)

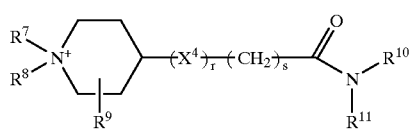

(3)

(In the formula 3, each of $R^7$ and $R^8$ represents an alkyl or alkenyl group having from 1 to 8 carbon atoms, wherein $R^7$ and $R^8$ may be the same or different from each other, $R^9$ represents hydrogen or an alkyl or alkenyl group having from 1 to 8 carbon atoms, each of $R^{10}$ and $R^{11}$ represents hydrogen or an alkyl or alkenyl group having from 1 to 25 carbon atoms (excluding a case in which $R^{10}$ and $R^{11}$ are both hydrogen), wherein $R^{10}$ and $R^{11}$ may be the same or different from each other, $X^4$ represents —O— or —S—, r is 0 or 1 and s is 0 or an integer of from 1 to 10.)

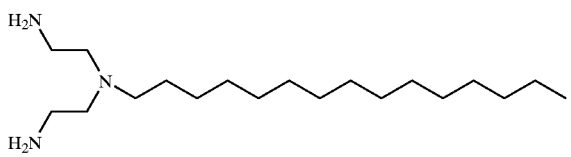

(4)

The aforementioned lipid derivative of a hydrophilic polymer is preferably a lipid derivative of polyethylene glycol, more preferably, said lipid derivative of polyethylene glycol is a compound which contains a polyethylene glycol chain and a diacyl glycerol in one molecule.

It is desirable that the aforementioned hydrophilic polymer has a molecular weight of from 1,000 to 7,000.

Regarding the aforementioned liposome, it is desirable that its major particle size range is from 90 to 200 nm.

It is desirable that the aforementioned drug to be included in the liposome is a drug for use in the diagnosis and/or treatment of renal diseases or a drug for use in the diagnosis and/or treatment of diseases which accompany overproduction of proteoglycan in injured portions of tissues and/or organs.

It is desirable that the aforementioned drug for use in the diagnosis and/or treatment of renal diseases is an adrenocortical steroid and/or a derivative thereof.

It is desirable to use the aforementioned liposome as a drug for the treatment of inflamed kidney, and it is desirable to produce a medicament for the treatment of inflamed kidney making use of such liposomes.

The invention also provides a method for the treatment of inflamed kidney, which comprises administering these liposomes to mammals including human.

BEST MODE FOR CARRYING OUT THE INVENTION

Figure 1:
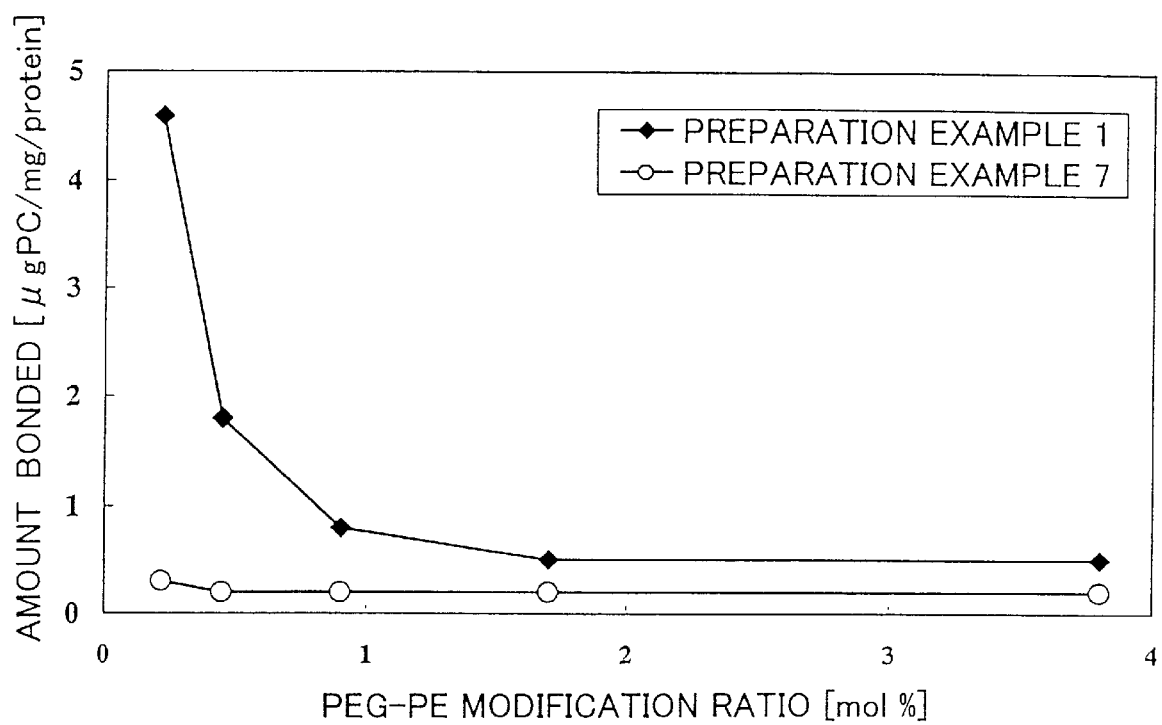
FIG. 1 is a graph showing a relationship between liposomes modified by a basic compound which takes positive charge within a physiological pH range and a hydrophilic polymer lipid derivative and their affinity for rat mesangial cells as proteoglycan producing cells.

The following describes the invention in detail.

The membrane constituting components of the liposome of the invention are comprised of a basic compound which takes positive charge within a physiological pH range, a hydrophilic polymer lipid derivative and a liposome constituting lipid, and it is possible to use a stabilizing agent, antioxidant and the like as occasion demands.

The liposome constituting lipid is not particularly limited, with the proviso that it can form liposome, but a phospholipid or a derivative thereof or a lipid other than phospholipid or a derivative thereof can be used suitably from the viewpoint of providing liposomes which are stable in the living body.

Examples of the aforementioned phospholipid include natural or synthetic phospholipids such as phosphatidylcholine (lecithin), phosphatidylglycerol, phosphatidic acid, phosphatidylethanolamine, phosphatidylserine, phosphatidylinositol, sphingomyelin, cardiolipin and the like, or their hydrogenated products obtained in the usual way.

Examples of the stabilizing agent include a sterol which reduces membrane fluidity, such as cholesterol; and saccharides such as glycerol and sucrose.

Examples of the antioxidant include a tocopherol homologue, namely vitamin E. Tocopherol exists in 4 isomer forms of $\alpha$, $\beta$, $\gamma$, and $\delta$, all of them can be used in the invention.

The liposome of the invention contains a basic compound which takes positive charge within a physiological pH range (sometimes to be referred to as basic compound hereinafter) and a hydrophilic polymer lipid derivative as membrane constituting components. The physiological pH range cannot be defined, because it varies depending on the condition of the living body, but it is a range of from 7.0 to 7.5 for example.

The basic compound which takes positive charge within a physiological pH range on the liposome surface is not particularly limited, with the proviso that it does not spoil structural stability of the liposome, and its examples include lipid derivatives in which a basic compound having an aliphatic primary amino group, an aliphatic secondary amino group, an aliphatic tertiary amino group, an aliphatic quaternary amino group; an amidino group; a guanidino group; an aromatic primary amino group, an aromatic secondary amino group, an aromatic tertiary amino group or an aromatic quaternary amino group is linked, directly through these groups or via an appropriate spacer, to a hydrophobic compound such as a long chain aliphatic alcohol, a sterol, a polyoxypropylene alkyl or a glycerol fatty acid ester. When linked to a hydrophobic compound, the portion which takes positive charge within a physiological pH range can easily be positioned on the surface of liposome. Among these compounds, a basic compound which has an amidino group, a basic compound which has two or more amino groups, a basic compound which has a piperidine ring or a basic compound which has a quaternary amine is preferable in terms of the strong mutual reaction.

In this connection, when these basic compounds are linked to hydrophobic compounds via a phosphate group or the like substituent group which takes negative charge within a physiological pH range (e.g., diacylglycerophosphatidylcholine, diacylglycerophosphatidylethanolamine and a derivative of diacylglycerophosphatidylethanolamine in which a neutral or negative substituent group is linked to the ethanolamine substituent group via an amido bond), the resulting compounds are neutrally or negatively charged within the physiological pH range due to such negative charge so that, as a matter of course, they are not included in the basic compound which takes positive charge within a physiological pH range.

These basic compounds may be used alone or as a mixture of two or more. Illustrative examples of the aforementioned compounds include DOTMA (U.S. Pat. No. 61,161,246), DOTAP (U.S. Pat. No. 5,508,626), Transfectam (U.S. Pat. No. 2,292,246), TMAG (U.S. Pat. No. 4,108,391), DOSPA, TfxTM-50, DODAC, DC-CHOL, DMRIE and the like known compounds. As more preferred examples, those in which the basic compound is any one of the aforementioned formulae 1 to 4 can be cited.

Amount of the basic compound which takes positive charge within a physiological pH range is preferably from 1 to 20 mol % based on the liposome constituting lipid, namely other membrane constituting component excluding said basic compound and the hydrophilic polymer. The amount if less than 1 mol % would entail poor accumulation on proteoglycan producing tissues and/or organs and if exceeding 20 mol % would spoil physical stability of liposomes in the living body.

Also, amount of the basic compound which takes positive charge within a physiological pH range is more preferably from 5 to 15 mol % based on the liposome constituting lipid, namely other membrane constituting component excluding said basic compound and the hydrophilic polymer. Within this range, selectivity for proteoglycan, particularly proteoglycan chondroitin sulfate, becomes excellent, and accumulation on the tissues and/or organs which produce proteoglycan chondroitin sulfate becomes particularly excellent.

Since the surface of the liposome of the invention takes positive charge within a physiological pH range, its accumulation on the tissues and/or organs which produce proteoglycan is expressed thereby.

Also, since the liposome of the invention is modified by a hydrophilic polymer, its stability in blood and RES avoiding effect are thereby obtained.

Various methods can be cited without particular limitation for modifying the liposome surface by a hydrophilic polymer, but it is desirable to employ a method in which said hydrophilic polymer is linked to a hydrophobic compound such as a long chain aliphatic alcohol, a sterol, a polyoxypropylene alkyl, a glycerol fatty acid ester or a phospholipid, and the portion of said hydrophobic compound is inserted into the liposome membrane.

The lipid derivative of hydrophilic polymer is not particularly limited, with the proviso that it does not spoil structural stability of the liposome, and its examples include lipid derivatives of polyethylene glycol, dextran, pullulan, Ficoll, polyvinyl alcohol, a styrenemaleic anhydride alternating copolymer, a divinyl ethermaleic anhydride alternating copolymer, a synthetic polyamino acid, amylose, amylopectin, chitosan, mannan, cyclodextrin, pectin, carrageenan and the like, of which polyethylene glycol and a lipid derivative of polyethylene glycol are particularly preferable.

The lipid derivative of polyethylene glycol is not particularly limited, but it is preferably a compound which contains a polyethylene glycol chain and a diacyl glycerol in one molecule.

It is desirable that the hydrophilic polymer has a molecular weight of from 1,000 to 7,000.

Particularly, polyethylene glycol and a lipid derivative of polyethylene glycol having a molecular weight of from 1,000 to 7,000 are desirable because of their significant effect to improve the retention in blood circulation.

Blending amount of the hydrophilic polymer lipid derivative is preferably from 0.2 to 5 mol % based on the total amount of the basic compound which takes positive charge within a physiological pH range and the liposome constituting lipid, though it varies depending on its molecular weight and adding method. Within this range, accumulation on the tissues and/or organs where proteoglycan is produced.

The reason for this is as follows. When blending amount of the hydrophilic polymer lipid derivative is within the above range, interaction between plasma protein and liposome is inhibited by hydrophilic polymer on the liposome surface, so that the stability in blood becomes excellent. On the other hand, when blending amount of the hydrophilic polymer lipid derivative is within the above range, binding of liposome with certain biological polymer components is not inhibited. Chondroitin sulfate, dermatan sulfate and the like as constituting components of proteoglycan belong to galactosaminoglycan (GAG) which is a fibrous anionic biological polymer component, but binding of such a fibrous anionic biological polymer with the liposome is not inhibited by the specified blending amount of the hydrophilic polymer lipid derivative of the invention. The liposome of the invention selectively recognizes a tissue and/or organ where proteoglycan having such GAG is produced.

An effect has been well known that concentration of liposomes in blood is maintained for a certain period of time by such modification by a hydrophilic polymer. On the other hand, the hydrophilic polymer lipid derivative has an aspect that it makes the surface of liposome hydrophilic and thereby diminishes its accumulation on organs. However, it has not been known that characteristics of the liposome surface are not diminished when modified by a hydrophilic polymer and that its characteristics can rather be improved through modification by the hydrophilic polymer within a certain range of concentration.

For example, a liposome in which the other lipid, a basic compound which takes positive charge within a physiological pH range and a hydrophilic polymer lipid derivative are blended within the range of 20:1:1 is disclosed in *Biochemistry*, 37: 12875, (1998). It is described in this report that, when about 5 mol % of a hydrophilic polymer which itself is anion and the same amount of a basic compound are blended, binding of cationic liposome to cells is inhibited by the hydrophilic polymer, but it does not describe that a liposome which has excellent stability in blood and binds to cells via its interaction with proteoglycan can be prepared by the blending ratio of the present invention.

Also, it has been reported in *Biochimica et Biophysica Acta*, 1326: 236, (1997) that interaction between a liposome which is not cationic and cells is inhibited by the blending of 1 to 5 mol % of a hydrophilic polymer lipid derivative. However, as shown in Test Example 1, the interaction between a cationic liposome and cells is completely different from the case of a neutral or anionic liposome, and binding strength of the cationic liposome to cells increases as the blending ratio of a basic compound which takes positive charge within a physiological pH range is increased (Test Examples 3 and 4), so that the just cited report in which such points are not examined is of no help with regard to the blending ratio of the hydrophilic polymer most suited for the interaction between the cationic liposome and cells.

A cationic liposome in which a PEG ceramide is blended as a hydrophilic polymer lipid derivative is disclosed in WO 96/10391. In this document, it is disclosed that the stability in blood is maintained by the blending of 10 mol % or more of the PEG ceramide in the case of a liposome which contains a basic compound that takes positive charge within a physiological pH range in an amount of about 17.5 mol % based on other lipids (about 15 mol % of the total lipids), and that its interaction with cells is maintained (retained), by the blending of 5 mol % of as the PEG ceramide. However, it does not disclose that a liposome in which its stability in blood is maintained and its interaction with cells via proteoglycan is optimized can be prepared by the blending ratio of the present invention (blending of from 1 to 20 mol %, preferably from 5 to 15 mol %, of a basic compound with from 0.2 to 5 mol % of a hydrophilic polymer derivative, based on other lipids).

WO 98/51285 discloses a liposome which contains a basic compound which takes positive charge within a physiological pH range and a combined product of PEG and dilauroylphosphatidylethanolamine or a liposome which contains diphthanoylphosphatidylethanolamine in addition to the basic compound and PEG derivative. According to the basic compound of this liposome, its content of 50% based on other lipids is disclosed, but nothing is disclosed about the blending ratio within the range of the present invention.

According to this invention, the blending ratio of the basic compound which takes positive charge within a physiological pH range and the hydrophilic polymer lipid derivative is a definitely important factor. Regarding the stability of liposomes in blood in particular, their interaction with plasma protein and incorporation into the RES system via the interaction have been regarded as important but, in addition to these factors, their interaction with fibrous anionic biological polymer components such as GAGs and the like which are constituting components of proteoglycan on the cell surface is important in the case of cationic liposomes.

In the case of glomerulonephritis, mesangial cells of the glomeruli generate a proliferative change and thereby cause the progression of disease. In Test Example 1, mesangial cell-binding ability of a liposome containing 8.7 mol % of a basic compound (3,5-dipentadecyloxybenzamidine hydrochloride) based on the other lipids is shown in comparison with a liposome which does not contain the basic compound. The liposome binds to mesangial cells only in the presence of the basic compound. Also, as shown in Test Example 2, this binding does not occur when GAGs linked to proteoglycan on the cell surface are cut out, thus showing that this binding is effected via the GAGs of proteoglycan. In addition, it is shown in Test Example 1 that, since the binding ability decreases as the amount of the hydrophilic polymer to be added is increased, it is desirable that the blending amount of the hydrophilic polymer does not exceed 5 mol %.

On the other hand, it is shown in Test Example 4 that, when the hydrophilic polymer is 5 mol % or less, aggregation in blood cannot sufficiently be inhibited if the basic compound which takes positive charge within a physiological pH range is blended in an amount exceeding 20 mol % based on other lipids. That is, it is desirable that blending ratio of the basic compound is set to 20 mol % or less based on other lipids.

Certain types of proteoglycan exist also in endothelial cells which cover the surface of blood vessels. In consequence, when interaction with such endothelial cells is strong, physical stability of liposomes in blood circulation is spoiled by this interaction with endothelial cells, thus arising a possibility of the inhibition of efficient delivery to an injured portion. Thus, it is more desirable that the liposome of interest can bind to proteoglycan in the injured portion but does not interact with proteoglycan on vascular endothelial cells. Surprisingly, it was revealed by some studies carried out by the present inventors based on Test Examples 3 and 4 that such a liposome can be realized when the basic compound is used at a blending ratio of between 1 mol % or more and 20 mol % or less, preferably 5 mol % or more and 15 mol % or less, based on other lipids.

As described above, the liposome which can bind to injured portions of tissues and/or organs where proteoglycan is produced, while maintaining its stability in blood, can be realized for the first time by the extremely limited ranges of blending ratios of a cationic lipid and a hydrophilic polymer, so that the liposome of the invention is clearly different from already known liposomes in terms of the construction and purpose.

According to the invention, a surface modifying agent other than the hydrophilic polymer lipid derivative can be used jointly. Examples of the surface modifying agent other than the hydrophilic polymer include water-soluble polysaccharides such as glucuronic acid, sialic acid and the like.

As the drug to be included in the liposome, pharmaceutically acceptable pharmacologically active substances, physiologically active substances and/or substances for diagnosis use can be used depending on each purpose for the diagnosis and/or treatment of renal diseases and other diseases that accompany overproduction of proteoglycan in injured portions of tissues and/or organs.

Properties of the drug to be included in the liposome are not particularly limited, but electrically neutral or anionic property is desirable, because the surface of liposome is modified by a substituent group which takes positive charge within a physiological pH range, and high inclusion ration can therefore be obtained.

Types of the drug to be included in the liposome are not particularly limited so far as the formation of liposome is not spoiled. Their examples include adrenocortical steroids such as prednisolone, methylprednisolone, dexamethasone and the like; non-steroidal anti-inflammatory drugs such as aspirin, indometacin, ibuprofen, mefenamic acid, phenylbutazone and the like; mesangial cell growth inhibitors such as heparin, low molecular weight heparin and the like; immunosuppressants such as cyclosporin and the like; angiotensin converting enzyme (ACE) inhibitors such as captopril and the like; AGE (advanced glycation endoproduct) inhibitors such as methylguanidine and the like; TGF-β antagonists such as biglycan, decorin and the like; PKC (protein kinase C) inhibitors; prostaglandin preparations such as $PGE_1$, $PGI_2$ and the like; peripheral vasodilators such as papaverine drugs, nicotinic acid drugs, tocopherol drugs, Ca antagonist and the like; phosphodiesterase inhibitors; anti-thrombus agents such as ticlopidine, aspirin and the like; anticoagulants such as warfarin, heparin, anti-thrombin agent and the like; thrombolytic agents such as urokinase and the like; chemical mediator release inhibitors; antibiotics; antioxidants; enzyme preparations; lipid incorporation inhibitors; hormone preparations; vitamin C; vitamin E; radical scavengers such as SOD and the like; antisense oligonucleotides which have the action to inhibit growth of mesangial cells; carcinostatic agents; decoys or genes; X-ray contrast media; radioisotope-labeled nuclear medicinal diagnostic agents; and MRI contrast media. Particularly, an adrenocortical steroid and/or a derivative thereof and/or a mixed preparation thereof containing other components can be suitably used by this invention. Because, despite their strong efficacy, they cause considerably strong systemic side effects. The continuous or long-term administration by this invention can minimize the side effect.

Examples of the diseases in which proteoglycan is excessively produced in the injured portions of tissues and/or organs include renal diseases in which inflammation is formed on glomeruli, as well as diseases in which fibrosis occurs in the liver, the lungs, the heart, the pancreas, the bone marrow, arteries and the like, the tumors such as large bowel cancer and the like and inflammatory diseases.

Examples of the aforementioned renal diseases include minimal change type focal glomerular sclerosis, IgA nephritis, mesangial proliferative glomerulonephritis, membranous glomerulonephritis, membranoproliferative glomerulonephritis types I, II and III, intracanalicular proliferative glomerulonephritis and crescentic glomerulonephritis (=extracapillary proliferative glomerulonephritis) as primary glomerulonephritis; and lupus nephritis, Goodpasture syndrome, diabetic nephropathy, systemic vascular inflammation, thrombotic microvascular inflammation, intraglomerular thrombosis, benign nephrosclerosis, malignant nephrosclerosis, progressive systemic sclerosis (scleroderma), glomerular disorder accompanied by infection and drug induced renal disorder as tonic glomerulonephritis.

Most suitable size of the liposome of the invention is from 90 to 200 nm as the major particle size range. As will be shown later in Test Example 8, the liposome if within this range can be easily transferred into inflamed tissues and/or organs accompanied by vascular damage and production of proteoglycans including renal glomeruli. The major particle size range if less than 90 nm would facilitate its transfer into normal tissues and/or organs too and if exceeding 200 nm would hinder smooth transfer into injured tissues. On the other hand, average particle size is an average value of total particle size measured by the light scattering method in the same manner, and this value is a value within the major particle size range and its range is preferably from 90 to 200 nm as a matter of course.

The liposome of the invention can be obtained easily in the usual way. An example thereof is shown in the following.

A basic compound which takes positive charge within a physiological pH range and other membrane constituting components such as a phospholipid, a stabilizing agent, an antioxidant and the like are mixed in organic solvent such as chloroform or the like in a flask, the solvent is evaporated and then the resulting residue is dried in vacuo to effect formation of a thin film on the inner wall of the flask. Next, a drug is put into the flask and vigorously stirred, thereby obtaining a liposome dispersion liquid. The thus obtained liposome dispersion liquid is centrifuged, and the supernatant is subjected to decantation to remove the un-trapped drug. Thereafter, the liposome of the invention is obtained by adding a hydrophilic polymer lipid derivative solution and heating the mixture. In this connection, the liposome of the invention can also be obtained by adding the hydrophilic polymer lipid derivative solution at the time of the mixing of membrane constituting components. Though both of these methods for adding the hydrophilic polymer lipid derivative solution do not have particular problems, the adding method at the time of the mixing of membrane constituting components entails inclusion of the hydrophilic polymer inside the liposome too, so that it will sometimes cause substantial reduction of the surface modification ratio and reduction of inclusion volume.

Alternatively, the liposome of the invention can also be obtained by mixing the aforementioned respective constituting components and effecting high pressure discharge of the mixture using a high pressure discharge type emulsifier.

The liposome of the invention specifically accumulates on proteoglycan producing tissues and/or organs, particularly on renal glomeruli which are caused inflammation by injury. The ratio of the accumulated amount of the liposome of the invention on injured tissues and/or organs to its accumulated amount on normal tissues and/or organs is approximately from 2 to 10 times when compared after its administration or after a certain lapse of time. In consequence, the use of the liposome of the invention renders possible efficient delivery of a drug to injured proteoglycan-overproducing tissues and/or organs, particularly to injured renal glomeruli, and its continuous action therein. In addition, even if a drug having large side effects is used as the drug, its side effects can be reduced to the minimum, so that when an adrenocortical steroid and/or a derivative thereof is used for example, the liposome can be used suitably for IgA nephritis or the like glomerulonephritis.

EXAMPLES

The following illustratively describes the invention with reference to examples, but the invention is not limited thereto.

1. Preparation of Various Types of Liposomes

Preparation Example 1

Preparation of a Liposome which Contains 3,5-Dipentadecyloxybenzamidine Hydrochloride and a Hpolyethylene Glycol-phosphatidylethanolamine Derivative (PEG-PE) as Membrane Constituting Components Each of the following 3 membrane constituting components was added as chloroform solution to a 50 ml capacity eggplant type flask and mixed.

Phosphatidylcholine (concentration, 100 mM): 3.0 ml

Cholesterol (concentration, 100 mM): 2.54 ml 3,5-Dipentadecyloxybenzamidine hydrochloride represented by the following formula (100 mM): 4.6 ml

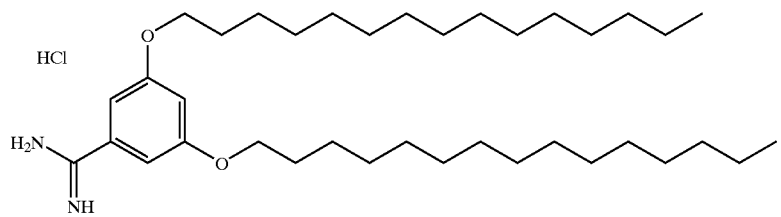

After evaporation of chloroform, the resulting residue was dried overnight in vacuo to effect formation of a lipid thin film on the inner wall of the flask. Next, 10 ml of 150 mM sodium chloride solution was put into the flask and treated with a bath type sonicator to obtain a liposome (MLV) dispersion liquid. This was compressed using a polycarbonate film of 0.4 μm in pore size and then compressed using a polycarbonate film of 0.1 μm to carry out dressing of grain.

The same volume of a solution prepared by dissolving a polyethylene glycol-phosphatidylethanolamine derivative represented by the following formula in physiological saline (concentration, 0.0125, 0.025, 0.05, 0.1, 0.2 or 0.4 w/v %) was added to the liposome dispersion liquid, and the mixture was heated at 60° C. for 30 minutes to obtain a dispersion liquid of the title liposome whose surface was modified by the hydrophilic polymer lipid derivative.

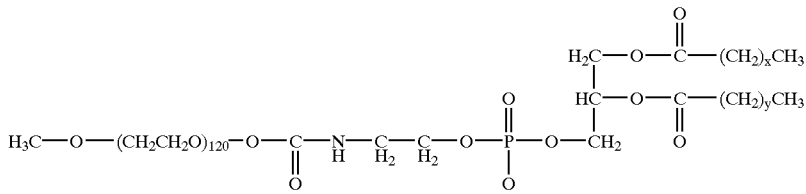

When a 100 μl portion of the thus obtained liposome dispersion liquid was dispersed in 3 ml of 150 mM sodium chloride aqueous solution and the particle size was measured using a particle size distribution analyzer Zetamaster-S manufactured by Malvern, the average particle size was from 127.1 to 132.5 nm and the major particle size range was from 90 to 200 nm.

Also, when the phosphatidylcholine content was measured by a choline oxidase method, and the cholesterol content by a cholesterol oxidase-phenol method and the 3,5-dipentadecyloxybenzamidine hydrochloride content by a liquid chromatography, the 3,5-dipentadecyloxybenzamidine hydrochloride content was 8.7 mol % based on other lipids.

Separately, the thus obtained liposome dispersion liquid was centrifuged at 100,000 g, and the supernatant was separated by decantation. The polyethylene glycol-phosphatidylethanolamine derivative (PEG-PE) content of the supernatant was measured by a picric acid reagent color developing method, and modification ratio of the PEG-PE derivative was calculated by subtracting the measured value from its added amount. The PEG-PE derivative modification ratio of the thus obtained liposomes were 0.11, 0.23, 0.45, 0.91, 1.8 and 3.8 mol %, respectively.

Preparation Example 2

Preparation of a Liposome which Contains N,N-Dioctadecyl-2-(Piperidin-4-yl-oxy)acetamide and a Polyethylene Glycol-phosphatidylethanolamine Derivative as Membrane Constituting Components Each of the following 3 membrane constituting components was added as chloroform solution to a 50 ml capacity eggplant type flask and mixed.

Phosphatidylcholine (concentration, 100 mM): 3.0 ml
Cholesterol (concentration, 100 mM): 2.54 ml
N,N-Dioctadecyl-2-(piperidin-4-yl-oxy)acetamide represented by the following formula (10 mM): 4.6 ml Thereafter, a dispersion liquid of the title liposome was obtained by the same method of Preparation Example 1.

When the thus obtained liposome was measured in the same manner as described in Preparation Example 1, the average particle size was from 112.4 to 127.8 nm, the major particle size range was from 90 to 200 nm, the N,N-dioctadecyl-2-(piperidin-4-yl-oxy)acetamide content was 8.7 mol % based on other lipids, and the PEG-PE derivative modification ratios were 0.11, 0.23, 0.45, 0.91, 1.8 and 3.8 mol %, respectively.

Preparation Example 3

Preparation of a Liposome which Contains N'-Pentadecyldiethylenetriamine and a Polyethylene Glycol-phosphatidylethanolamine Derivative as Membrane Constituting Components Each of the following 3 membrane constituting components was added as chloroform solution to a 50 ml capacity eggplant type flask and mixed.

Phosphatidylcholine (concentration, 100 mM): 3.0 ml
Cholesterol (concentration, 100 mM): 2.54 ml
N'-Pentadecyldiethylenetriamine represented by the following formula (10 mM): 4.6 ml

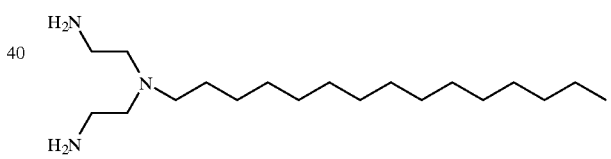

Thereafter, a dispersion liquid of the title liposome was obtained by the same method of Preparation Example 1.

When the thus obtained liposome was measured in the same manner as described in Preparation Example 1, the average particle size was from 111.7 to 125.8 nm, the major particle size range was from 90 to 200 nm, the N'-pentadecyldiethylenetriamine content was 8.7 mol % based on other lipids, and the PEG-PE derivative modification ratios were 0.11, 0.23, 0.45, 0.91, 1.8 and 3.8 mol %, respectively.

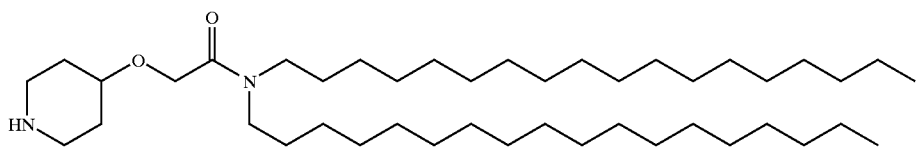

Preparation Example 4

Preparation of a Liposome which Contains Glucamine Palmitate and a Polyethylene Glycol-phosphatidylethanolamine Derivative as Membrane Constituting Components

Each of the following 3 membrane constituting components was added as chloroform solution to a 50 ml capacity eggplant type flask and mixed.

Phosphatidylcholine (concentration, 100 mM): 3.0 ml

Cholesterol (concentration, 100 mM): 2.54 ml

Glucamine palmitate represented by the following formula (10 mM): 4.6 ml

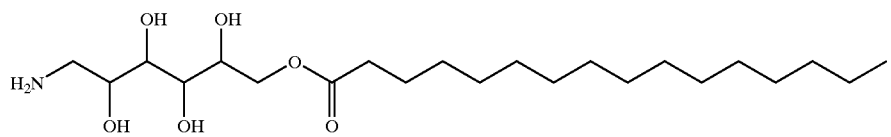

Thereafter, a dispersion liquid of the title liposome was obtained by the same method of Preparation Example 1.

When the thus obtained liposome was measured in the same manner as described in Preparation Example 1, the average particle size was from 112.5 to 124.5 nm, the major particle size range was from 90 to 200 nm, the glucamine palmitate content was 8.7 mol % based on other lipids, and the PEG-PE derivative modification ratios were 0.11, 0.23, 0.45, 0.91, 1.8 and 3.8 mol %, respectively.

Preparation Example 5

Preparation of a Liposome which Contains 1,2-Dipalmitoyl-3-trimethylammoniumpropane and a Polyethylene Glycol-phosphatidylethanolamine Derivative as Membrane Constituting Components

Each of the following 3 membrane constituting components was added as chloroform solution to a 50 ml capacity eggplant type flask and mixed.

Phosphatidylcholine (concentration, 100 mM): 3.0 ml

Cholesterol (concentration, 100 mM): 2.54 ml 1,2-Dipalmitoyl-3-trimethylarmoniwunpropane represented by the following formula (10 mM): 4.6 ml

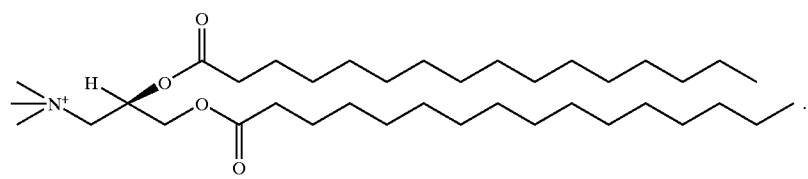

Thereafter, a dispersion liquid of the title liposome was obtained by the same method of Preparation Example 1.

When the thus obtained liposome was measured in the same manner as described in Preparation Example 1, the average particle size was from 113.4 to 130.1 nm, the major particle size range was from 90 to 200 nm, the 1,2-dipalmitoyl-3-trimethylammoniumpropane content was 8.7 mol % based on other lipids, and the PEG-PE derivative modification ratios were 0.11, 0.23, 0.45, 0.91, 1.8 and 3.8 mol %, respectively.

Preparation Example 6

Preparation of a Liposome which Contains 1,2-Dipalmitoyl-3-dimethylammoniumpropane and a Polyethylene Glycol-phosphatidylethanolamine Derivative as Membrane Constituting Components Each of the following 3 membrane constituting components was added as chloroform solution to a 50 ml capacity eggplant type flask and mixed.

Phosphatidylcholine (concentration, 100 mM): 3.0 ml

Cholesterol (concentration, 100 mM): 2.54 ml 1,2-Dipalmitoyl-3-dimethylammoniumpropane represented by the following formula (10 mM): 4.6 ml Thereafter, a dispersion liquid of the title liposome was obtained by the same method of Preparation Example 1.

When the thus obtained liposome was measured in the same manner as described in Preparation Example 1, the average particle size was from 113.4 to 130.1 nm, the major particle size range was from 90 to 200 nm, the 1,2-dipalmitoyl-3-dimethylammoniumpropane content was 8.7 mol % based on other lipids, and the PEG-PE derivative modification ratios were 0.11, 0.23, 0.45, 0.91, 1.8 and 3.8 mol %, respectively.

Preparation Example 7

Preparation of a Neutral Liposome Preparation

Each of the following 2 membrane constituting components was added as chloroform solution to a 50 ml capacity eggplant type flask and mixed.

Phosphatidylcholine (concentration, 100 mM): 3.48 ml

Cholesterol (concentration, 100 mM): 2.54 ml

Thereafter, a dispersion liquid of the title liposome was obtained by the same method of Preparation Example 1.

When the thus obtained liposome was measured in the same manner as described in Preparation Example 1, the average particle size was from 111.4 to 126.5 nm, the major particle size range was from 90 to 200 nm, and the PEG-PE derivative modification ratios were 0.11, 0.23, 0.45, 0.91, 1.8 and 3.8 mol %, respectively.

Preparation Example 8

Preparation of a Liposome which Contains 3,5-Dipentadecyloxybenzamidine Hydrochloride and a Polyethylene Glycol-phosphatidylethanolamine Derivative as Membrane Constituting Components Each of the following 3 membrane constituting components was added as chloroform solution to a 50 ml capacity eggplant type flask and mixed.

Phosphatidylcholine (concentration, 100 mM): 3.12 ml

Cholesterol (concentration, 100 mM): 2.66 ml 3,5-Dipentadecyloxybenzamidine hydrochloride (10 mM): 2.3 ml Thereafter, a dispersion liquid of the title liposome was obtained by the same method of Preparation Example 1.

When the thus obtained liposome was measured in the same manner as described in Preparation Example 1, the average particle size was from 124.5 to 132.4 nm, the major particle size range was from 90 to 200 nm, the 3,5-dipentadecyloxybenzamidine hydrochloride content was 4.2 mol % based on other lipids, and the PEG-PE derivative modification ratios were 0.11, 0.23, 0.45, 0.91, 1.8 and 3.8 mol %, respectively.

Preparation Example 9

Preparation of a Liposome which Contains 3,5-Dipentadecyloxybenzamidine Hydrochloride and a Polyethylene Glycol-phosphatidylethanolamine Derivative as Membrane Constituting Components Each of the following 3 membrane constituting components was added as chloroform solution to a 50 ml capacity eggplant type flask and mixed.

Phosphatidylcholine (concentration, 100 mM): 2.76 ml

Cholesterol (concentration, 100 mM): 2.36 ml 3,5-Dipentadecyloxybenzamidine hydrochloride (100 mM): 8.63 ml Thereafter, a dispersion liquid of the title liposome was obtained by the same method of Preparation Example 1.

When the thus obtained liposome was measured in the same manner as described in Preparation Example 1, the average particle size was from 113.3 to 123.2 nm, the major particle size range was from 90 to 200 nm, the 3,5-dipentadecyloxybenzamidine hydrochloride content was 17.6 mol % based on other lipids, and the PEG-PE derivative modification ratios were 0.11, 0.23, 0.45, 0.91, 1.8 and 3.8 mol %, respectively.

Preparation Example 10

Preparation of a Liposome which Contains 3,5-Dipentadecyloxybenzamidine Hydrochloride and a Polyethylene Glycol-phosphatidylethanolamine Derivative as Membrane Constituting Components Each of the following 3 membrane constituting components was added as chloroform solution to a 50 ml capacity eggplant type flask and mixed.

Phosphatidylcholine (concentration, 100 mM): 2.28 ml

Cholesterol (concentration, 100 mM): 1.94 ml 3,5-Dipentadecyloxybenzamidine hydrochloride (100 mM): 1.73 ml Thereafter, a dispersion liquid of the title liposome was obtained by the same method of Preparation Example 1.

When the thus obtained liposome was measured in the same manner as described in Preparation Example 1, the average particle size was from 125.3 to 133.3 nm, the major particle size range was from 90 to 200 nm, the 3,5-dipentadecyloxybenzamidine hydrochloride content was 42.9 mol % based on other lipids, and the PEG-PE derivative modification ratios were 0.11, 0.23, 0.91, 1.8 and 3.8 mol %, respectively.

Preparation Example 11

Preparation of a Liposome which Contains 1,2-Dipalmitoyl-3-trimethylammoniumpropane and a Polyethylene Glycol-phosphatidylethanolamine Derivative as Membrane Constituting Components Each of the following 3 membrane constituting components was added as chloroform solution to a 50 ml capacity eggplant type flask and mixed.

Phosphatidylcholine (concentration, 100 mM): 3.24 ml

Cholesterol (concentration, 100 mM): 2.75 ml 1,2-Dipalmitoyl-3-trimethylammoniumpropane (10 mM): 0.29 ml Thereafter, a dispersion liquid of the title liposome was obtained by the same method of Preparation Example 1.

When the thus obtained liposome was measured in the same manner as described in Preparation Example 1, the average particle size was from 115.4 to 126.3 nm, the major particle size range was from 90 to 200 nm, the 1,2-dipalmitoyl-3-dimethylammoniumpropane content was 0.5 mol % based on other lipids, and the PEG-PE derivative modification ratios were 0.11, 0.23, 0.91, 1.8 and 3.8 mol %, respectively.

Preparation Example 12

Preparation of a Liposome which Contains 1,2-Dipalmitoyl-3-trimethylammoniumpropane and a Polyethylene Glycol-phosphatidylethanolamine Derivative as Membrane Constituting Components Each of the following 3 membrane constituting components was added as chloroform solution to a 50 ml capacity eggplant type flask and mixed.

Phosphatidylcholine (concentration, 100 mM): 3.06 ml

Cholesterol (concentration, 100 mM): 2.66 ml 1,2-Dipalmitoyl-3-trimethylammoniumpropane (10 mM): 2.88 ml Thereafter, a dispersion liquid of the title liposome was obtained by the same method of Preparation Example 1.

When the thus obtained liposome was measured in the same manner as described in Preparation Example 1, the average particle size was from 114.5 to 128.1 nm, the major particle size range was from 90 to 200 nm, the 1,2-dipalmitoyl-3-dimethylammoniumpropane content was 5.3 mol % based on other lipids, and the PEG-PE derivative modification ratios were 0.11, 0.23, 0.91, 1.8 and 3.8 mol %, respectively.

Preparation Example 13

Preparation of a Liposome which, Contains N',N"-Dipentadecyltriethyltetramine and a Polyethylene Glycol-phosphatidylethanolamine Derivative as Membrane Constituting Components Each of the following 3 membrane constituting. components was added as chloroform solution to a 50 ml capacity eggplant type flask and mixed.

Phosphatidylcholine (concentration, 100 mM): 3.24 ml

Cholesterol (concentration, 100 mM): 2.75 ml

N',N"-Dipentadecyltriethyltetramine represented by the following formula (10 mM): 0.29 ml Thereafter, a dispersion liquid of the title liposome was obtained by the same method of Preparation Example 1.

When the thus obtained liposome was measured in the same manner as described in Preparation Example 1, the average particle size was from 111.4 to 123.1 nm, the major particle size range was from 90 to 200 nm, the N',N"-dipentadecyltriethyltetramine content was 0.5 mol % based on other lipids, and the PEG-PE derivative modification ratios were 0.11, 0.23, 0.91, 1.8 and 3.8 mol %, respectively.

Preparation Example 14

Preparation of a Liposome which Contains N',N"-Dipentadecyltriethyltetramine and a Polyethylene Glycol-phosphatidylethanolamine Derivative as Membrane Constituting Components Each of the following 3 membrane constituting components was added as chloroform solution to a 50 ml capacity eggplant type flask and mixed.

Phosphatidylcholine (concentration, 100 mM): 3.06 ml

Cholesterol (concentration, 100 mM): 2.66 ml

N',N"-Dipentadecyltriethyltetramine (10 mM): 2.88 ml

Thereafter, a dispersion liquid of the title liposome was obtained by the same method of Preparation Example 1.

When the thus obtained liposome was measured in the same manner as described in Preparation Example 1, the average particle size was from 122.5 to 130.5 nm, the major particle size range was from 90 to 200 nm, the N',N"-dipentadecyltriethyltetramine content was 5.3 mol % based on other lipids, and the PEG modification ratios were 0.11, 0.23, 0.91, 1.8 and 3.8 mol %, respectively.

Preparation Example 15

Preparation of a Liposome which Contains 3,5-Dipentadecyloxybenzamidine and a Polyethylene Glycol-phosphatidylethanolamine Derivative as Membrane Constituting Components and Includes Prednisolone Phosphate Sodium Therein Each of the following 4 membrane constituting components was added as chloroform solution to a 50 ml capacity eggplant type flask and mixed.

Phosphatidylcholine (concentration, 100 mM): 4.2 ml

Cholesterol (concentration, 100 mM): 1.20 ml 3,5-Dipentadecyloxybenzamidine hydrochloride (10 mM): 5.75 ml Polyethylene glycol-phosphatidylethanolamine derivative (1 mM): 12 ml After evaporation of chloroform, the resulting residue was dried overnight in vacuo to effect formation of a lipid thin film on the inner wall of the flask. Next, 10 ml of 10 mM sodium chloride aqueous solution containing 140 mM prednisolone phosphate sodium was put into the flask and treated with a bath type sonicator to obtain a liposome (MLV)

dispersion liquid. This was compressed using a polycarbonate film of 0.4 μm in pore size and then compressed using a polycarbonate film of 0.1 μm to carry out dressing of grain, thereby obtaining a dispersion liquid of the title liposome.

When the thus obtained liposome was measured in the same manner as described in Preparation Example 1, the average particle size was 133.1 nm and the major particle size range was from 90 to 200 nm.

Comparative Example 1

A liposome was prepared in the same manner as described in Preparation Example 15, except that physiological saline was used instead of the 10 mM sodium chloride aqueous solution containing 140 mM prednisolone phosphate sodium used in Preparation Example 15. The average particle size was 103.4 nm and the major particle size range was from 90 to 200 nm.

Preparation Example 16

Preparation of Liposome having an Average Particle Size of Exceeding 200 nm

A dispersion liquid of the title liposome was obtained in the same manner as described in Preparation Example 1, except that the polycarbonate film of 0.4 μm in pore size alone was used for the dressing of grain and the polycarbonate film of 0.1 μm in pore size was not used.

When particle size of the thus obtained liposome was measured in the same manner as described in Preparation Example 1, the average particle size was 273 nm and the major particle size range was from 180 to 350 nm.

Preparation Example 17

Preparation of Liposome having an Average Particle Size of Less than 90 nm

A dispersion liquid of the title liposome was obtained in the same manner as, described in Preparation Example 1, except that the dressing of grain was carried out using a polycarbonate film of 0.4 μm in pore size, a polycarbonate film of 0.1 μm in pore size and then a polycarbonate film of 0.05 μm in pore size.

When particle size of the thus obtained liposome was measured in the same manner as described in Preparation Example 1, the average particle size was 79.6 nm and the major particle size range was from 40 to 90 nm.

2. Test Examples on the Performance of Various Liposomes

Performances of the thus obtained various liposomes were tested.

Test Example 1

Affinity for Proteoglycan Producing Cells (1)

The purpose of this test is to know the effect of the surface modification by a basic compound which takes positive charge within a physiological pH range on the adhesion and incorporation of liposomes to and into proteoglycan producing cells, and the effect of a hydrophilic polymer lipid derivative on this case.
<Method>
Rat mesangial cells were cultured using a 12 well microplate until their proliferation reached about $4\times10^4$/well as the number of cells. Each of the Rhodamine-labeled liposomes prepared in accordance with Preparation Examples 1 and 7, in which the liposome membranes were labeled with Rhodamine-PE, was added to each well in an amount of 50 μg as lipid. After 24 hours of incubation at 37° C., the plate was washed twice with physiological saline. The cells were lysed by adding 0.1% SDS solution, and the fluorescence intensity was measured to calculate the amount of liposomes adhered to and incorporated into cells.
<Results>
The results are shown in FIG. 1.

When liposomes whose surfaces were modified by a basic compound which takes positive charge within a physiological pH range were further modified by various concentrations of a polyethylene glycol-phosphatidylethanolamine derivative, aggregation occurred during the test when they were not modified by the polyethylene glycol-phosphatidylethanolamine derivative. Also, adhesion to and incorporation into cells did not occur in the case of liposomes having no basic compound which takes positive charge within a physiological pH range on their surfaces.

That is, in order to ensure stable adhesion to and incorporation into proteoglycan producing cells, it is necessary that their surfaces are modified by the basic compound which takes positive charge within a physiological pH range, and it is necessary for more stable incorporation that the modifying amount of the hydrophilic polymer lipid derivative is 5 mol % or less.

Test Example 2

Affinity for Proteoglycan Producing Cells (2)

The purpose of this test is to know importance of proteoglycan for the adhesion of liposomes, in which their surfaces were modified by a basic compound which takes positive charge within a physiological pH range, to proteoglycan producing cells.
<Method>
Rat mesangial cells were cultured using a 12 well microplate until their proliferation reached about $4\times10^4$/well as the number of cells. Thereafter, they were enzymatically treated with chondroitinase ABC to remove proteoglycan from the cell surface.

Figure 2:
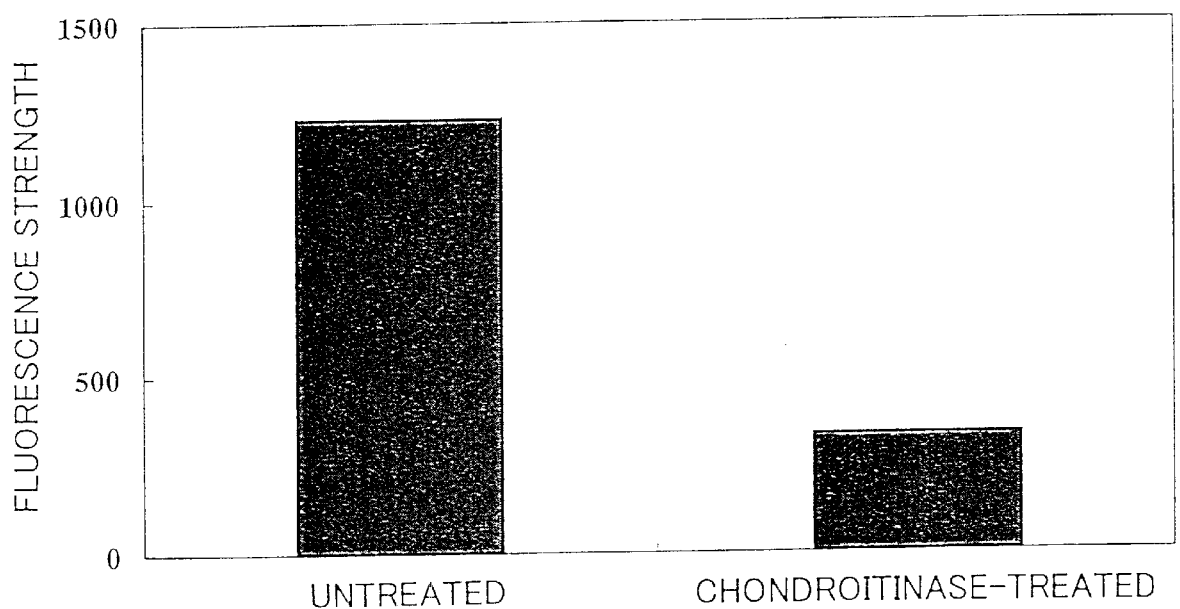
FIG. 2 is a graph showing participation of proteoglycan in the affinity of liposomes modified by a basic compound which takes positive charge within a physiological pH range and a hydrophilic polymer lipid derivative for rat mesangial cells as proteoglycan producing cells.

The Rhodamine-labeled liposome prepared in accordance with Preparation Examples 1 having a polyethylene glycol-phosphatidylethanolamine derivative modification ratio of 0.45 mol %, in which the liposome membrane was labeled with Rhodamine-PE, was added to each well in an amount of 50 μg as lipid. After 3 hours of incubation at 37° C., the plate was washed twice with physiological saline. The cells were lysed by adding 0.1% SDS solution, and the fluorescence intensity was measured to calculate the amount of liposomes adhered to and incorporated into cells.
<Results>
The results are shown in FIG. 2.

The liposomes whose surfaces were modified by a basic compound which takes positive charge within a physiological pH range adhered to the cells whose surfaces were covered with proteoglycan, but their adhesion to the treated cells in which chondroitin sulfate was cut out from proteoglycan by chondroitinase ABC was considerably reduced.

That is, a liposome whose surface is modified by a basic compound which takes positive charge within a physiological pH range adheres by binding to proteoglycan on the cell surface via chondroitin sulfate or the like GAG in the molecule.

Test Example 3

Affinity for Proteoglycan Producing Cells (3)

The purpose of this test is to know the effect of the surface-modifying amount of a basic compound which takes positive charge within a physiological pH range on the affinity for proteoglycan producing cells.
<Methods>

Rat mesangial cells were cultured using a 12 well microplate until their proliferation reached about $4\times10^4$/well as the number of cells. Each of the Rhodamine-labeled liposomes prepared in accordance with Preparation Examples 8, 1, 9 and 10, and 11 to 14, in which the liposome membranes were labeled with Rhodamine-PE, was added to each well in an amount of 50 μg as lipid. After 24 hours of incubation at 37° C., the plate was washed twice with physiological saline. The cells were lysed by adding 0.1% SDS solution, and the fluorescence intensity was measured to calculate the amount of liposomes adhered to and incorporated into cells.

In the same manner, human vascular endothelial cells were cultured using a 12 well microplate until their proliferation reached about $4\times10^4$/well as the number of cells, and each of the Rhodamine-labeled liposomes prepared in accordance with Preparation Examples 8, 1, 9 and 10, and 11 to 14, in which the liposome membranes were labeled with Rhodamine-PE, was added to each well in an amount of 50 μg as lipid. Thereafter, the amount of liposomes adhered to and incorporated into cells was calculated by repeating the same procedure of the case of rat mesangial cells.
<Results>

The results are shown in FIGS. 3 to 6.

Their adhesion to the cells varies depending on the amount of the basic compound which takes positive charge within a physiological pH range on the cell surface.

Figure 3:
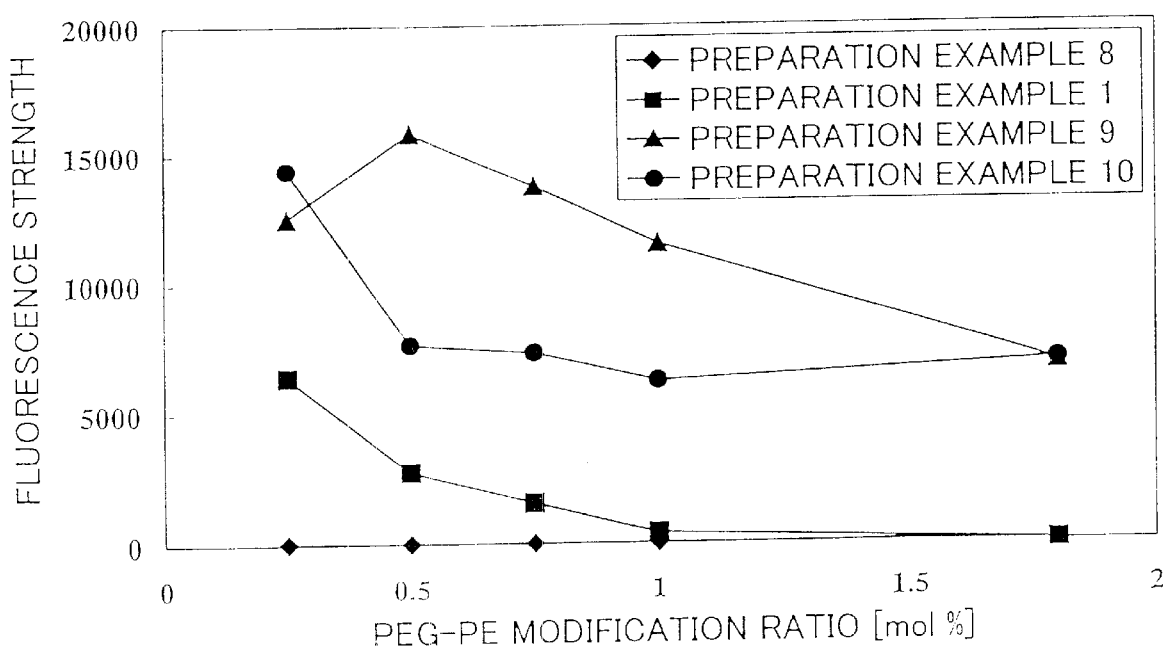
FIG. 3 is a graph showing a relationship between the amount of a basic compound which takes positive charge within a physiological pH range contained in the liposome constituting lipid and the affinity for rat mesangial cells.
Figure 4:
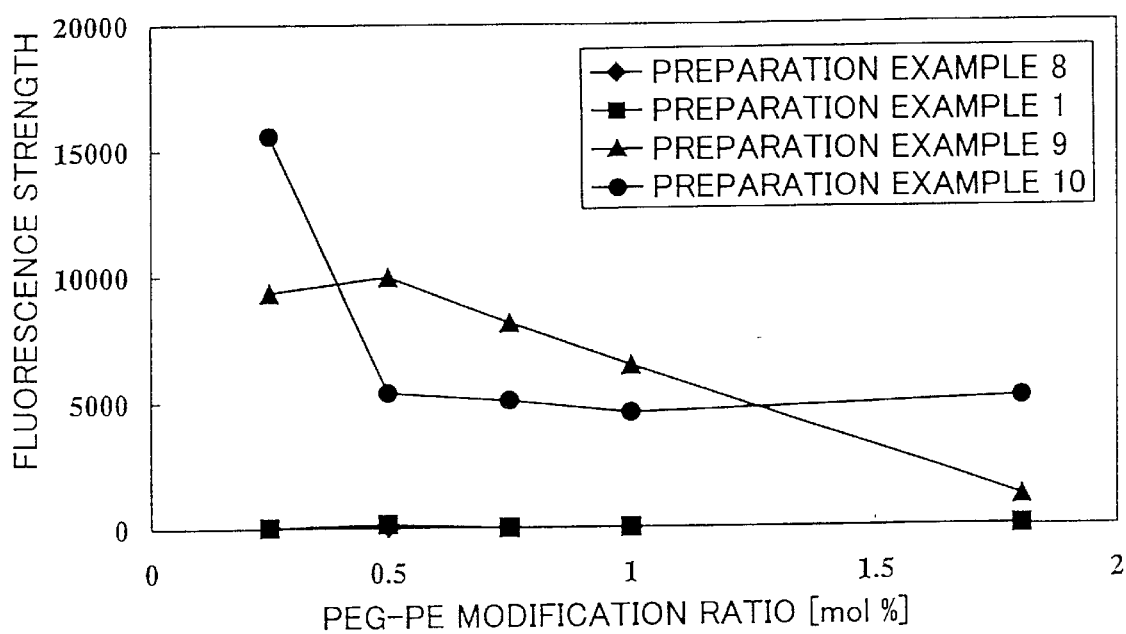
FIG. 4 is a graph showing a relationship between the amount of a basic compound which takes positive charge within a physiological pH range contained in the liposome constituting lipid and the affinity for human vascular endothelial cells.
Figure 5:
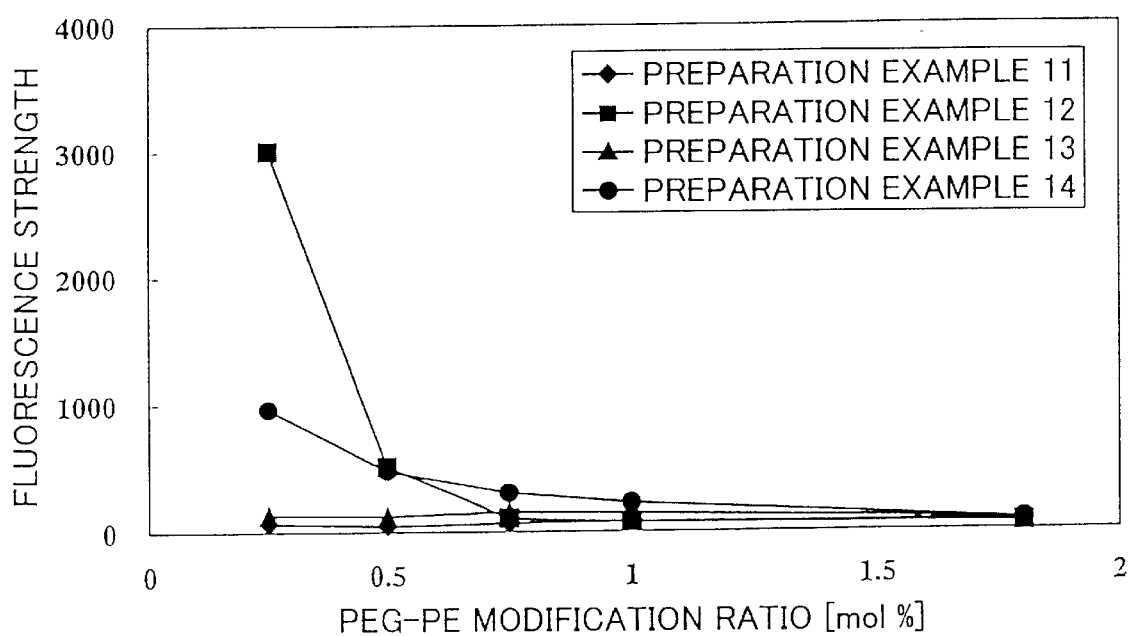
FIG. 5 is a graph showing a relationship between the amount of a basic compound which takes positive charge within a physiological pH range contained in the liposome constituting lipid and the affinity for rat mesangial cells.
Figure 6:
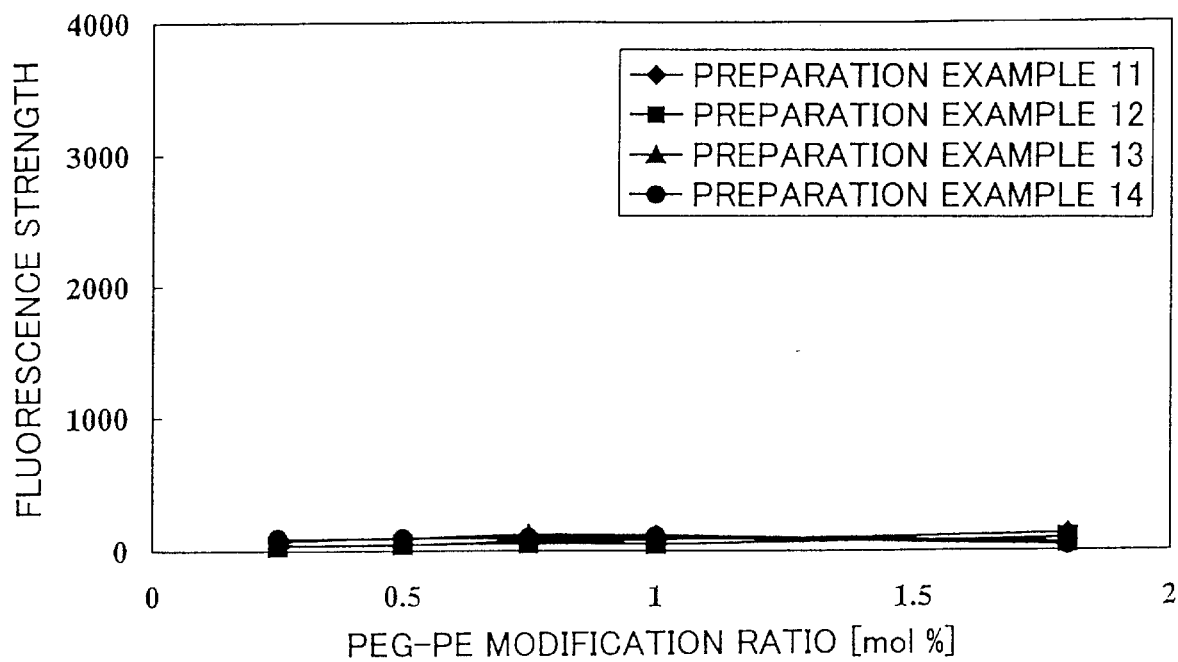
FIG. 6 is a graph showing a relationship between the amount of a basic compound which takes positive charge within a physiological pH range contained in the liposome constituting lipid and the affinity for human vascular endothelial cells.

Their adhesion to rat mesangial cells and human vascular endothelial cells did not occur when the basic compound content was 0.5 mol % or less, but the adhesion to rat mesangial cells capable of producing a large amount of chondroitin sulfate proteoglycan was improved when the content was 1 mol % or more (FIG. 3 and FIG. 5). Also, the adhesion to rat mesangial cells increases as the basic compound content was increased. However, when the content was increased to 20 mol % or more, the adhesion to human vascular endothelial cells capable of producing a large amount of heparan sulfate proteoglycan also increased (FIG. 4 and FIG. 5). Also, strength of the adhesion to mesangial cells varied depending on the kind of basic compound, and the adhesion was ensured generally at 5 mol % or more in each case of the membrane materials and the adhesion to mesangial cells was observed even within the range of from 1 to 5 mol % depending on the membrane material.

That is, the adhesion to proteoglycan producing cells occurs at a cationic membrane material content of 1 mol % or more. It is preferably 5 mol % or more. Also, when it is within the range of from 5 to 15 mol %, a liposome which does not bind to vascular endbthelial cells but shows adhesion selectively for proteoglycan produced by the target cells on an injured portion can be prepared, so that such a range is particularly desirable.

Test Example 4

Stability of Various Liposomes in Serum

The object of this test: is to know effect of the amount of liposome surface basic compound which takes positive charge within a physiological pH range on the stability of liposomes in serum.
<Method>

A 100 μl portion of rat serum was mixed with 100 μl of a dispersion liquid prepared by diluting each of the liposomes obtained in Preparation Examples 8, 1, 9 and 10 with physiological saline to 10 mM as the total lipid, and the mixture was incubated at 37° C. for 1 hour. After cooling, this was diluted by adding 2 ml of physiological saline, and its turbidity was measured at an absorbance of 450 nm.
<Results>

Figure 7:
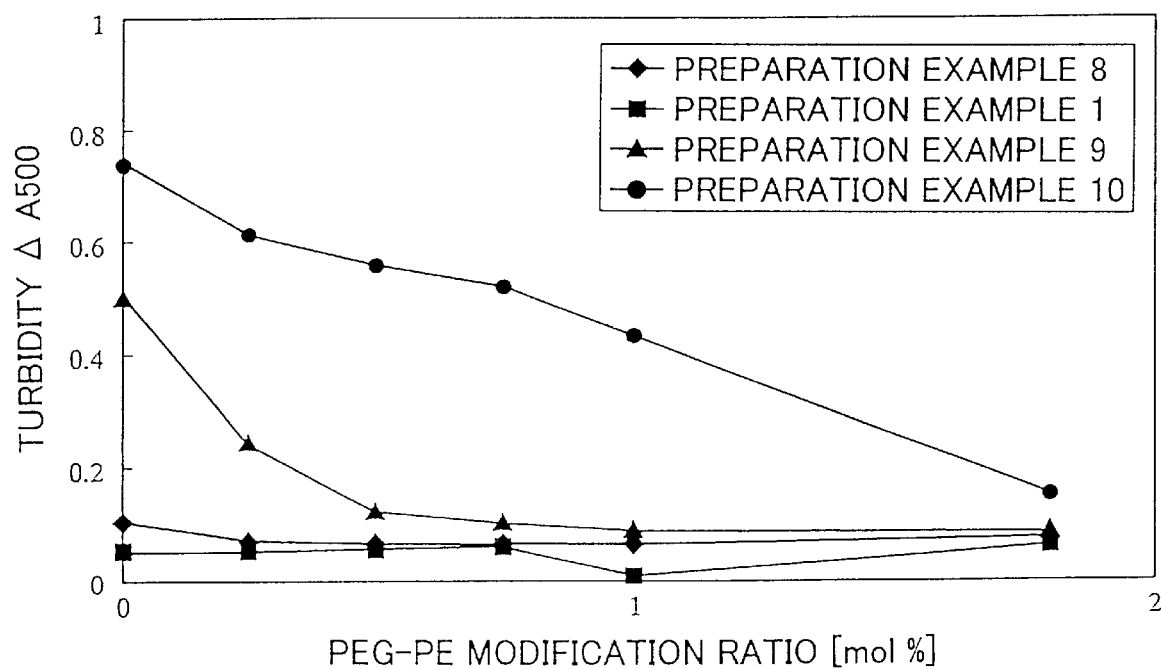
FIG. 7 is a graph showing a relationship between the amount of a basic compound which takes positive charge within a physiological pH range contained in the liposome constituting lipid and the stability of liposome in serum.

The results are shown in FIG. 7.

Aggregation of liposomes in serum varies depending on the amount of the basic compound which takes positive charge within a physiological pH range.

No problems were observed regarding their aggregation in serum when the basic compound content was 15 mol % or less. In the case of from 15 to 20 mol %, it was able to prevent their aggregation when the PEG-PE derivative-PE modification ratio was 0.5 mol % or more. When the basic compound content was increased to 20 mol % or more, aggregation of liposomes occurred and their stability was spoiled even by the addition of 2 mol % of the PEG-PE derivative-PE.

That is, in order to prevent aggregation of liposomes in blood and ensure their stability, it is most desirable to set the basic compound content to 20 mol % or less.

Test Example 5

Affinity of Various Liposomes for Proteoglycan

The object of this test is to know influence of a hydrophilic polymer lipid derivative upon the adhesion of proteoglycan to liposomes whose surfaces were modified by a basic compound which takes positive charge within a physiological pH range.
<Method>

Chondroitin sulfate C was dissolved in physiological saline to a concentration of 0.1 mg/ml. A 0.5 ml portion of this solution was mixed with 0.5 ml of each of the liposomes obtained in Preparation Example 1, which had been diluted with physiological saline to a total lipid concentration of 10 mM, and the mixture was incubated at 37° C. for 1 hour. After cooling, its turbidity was measured at an absorbance of 550 nm to examine influence of the polyethylene glycol-phosphatidylethanolamine derivative modification ratio upon the adhesion of chondroitin sulfate C based on the correlation between the turbidity and the polyethylene glycol-phosphatidylethanolamine derivative modification ratio.
<Results>

Figure 8:
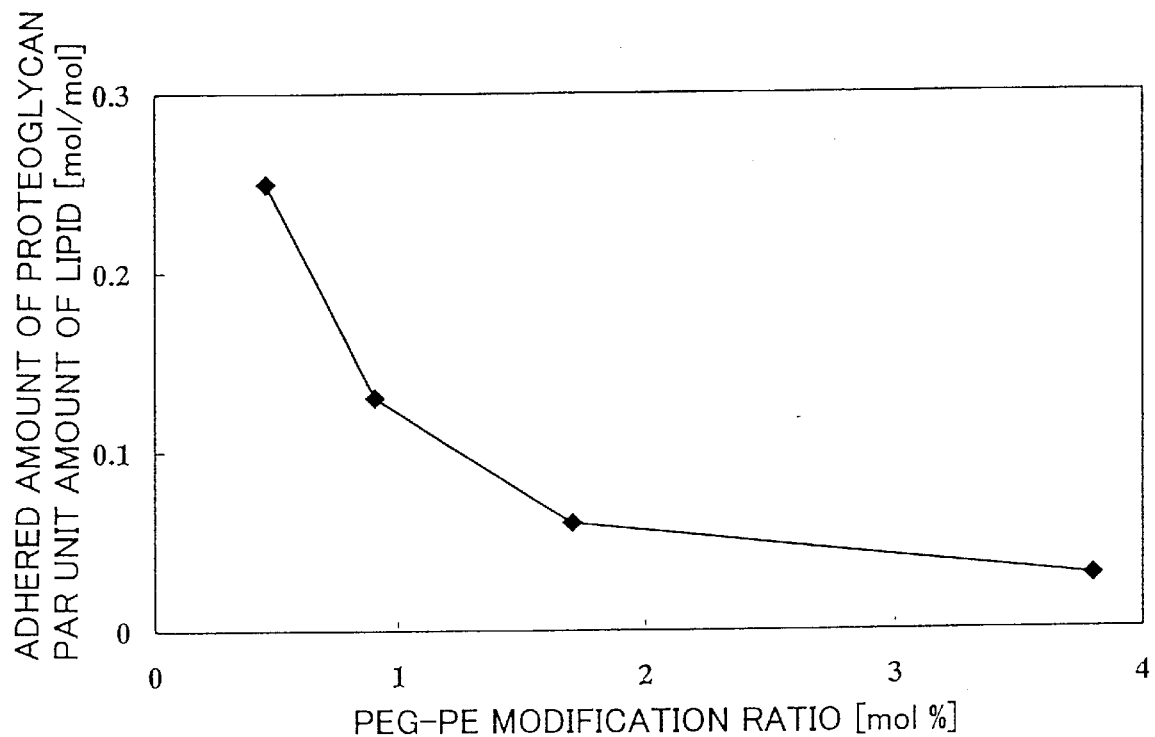
FIG. 8 is a graph showing a relationship between the modification by a hydrophilic polymer lipid derivative and the affinity for proteoglycan in a liposome modified by a basic compound which takes positive charge within a physiological pH range.

The results are shown in FIG. 8.

When modified by various concentration of the polyethylene glycol-phosphatidylethanolamine derivative, the adhered amount of proteoglycan increased as the modification concentration is reduced. Also, the adhesion of proteoglycan was effective when the modifying amount was 5 mol % or less.

That is, adhesion of proteoglycan to liposomes whose surfaces were modified by a basic compound which takes positive charge within a physiological pH range can be controlled by modifying the liposome surface by a hydrophilic polymer lipid derivative, and 5 mol % or less is most suitable for this purpose.

Test Example 6

Stabilization in Blood by Hydrophilic Polymer Lipid Derivative Modification

The object of this test is to know influence of the modification by a polyethylene glycol-phosphatidylethanolamine derivative upon the stability of liposomes in blood.

\<Method\>

A citrated human blood sample was centrifuged at 3,500 rpm for 15 minutes to obtain human blood plasma. A 1.95 ml portion of this human plasma was mixed with 0.05 ml of the liposome obtained in Preparation Example 4, and the mixture was incubated at 37° C. for 1 hour. After cooling, turbidity of the mixture was measured at an absorbance of 550 nm to calculate polyethylene glycol-phosphatidylethanolamine derivative modification ratio of the aggregated liposomes.

\<Results\>

Figure 9:
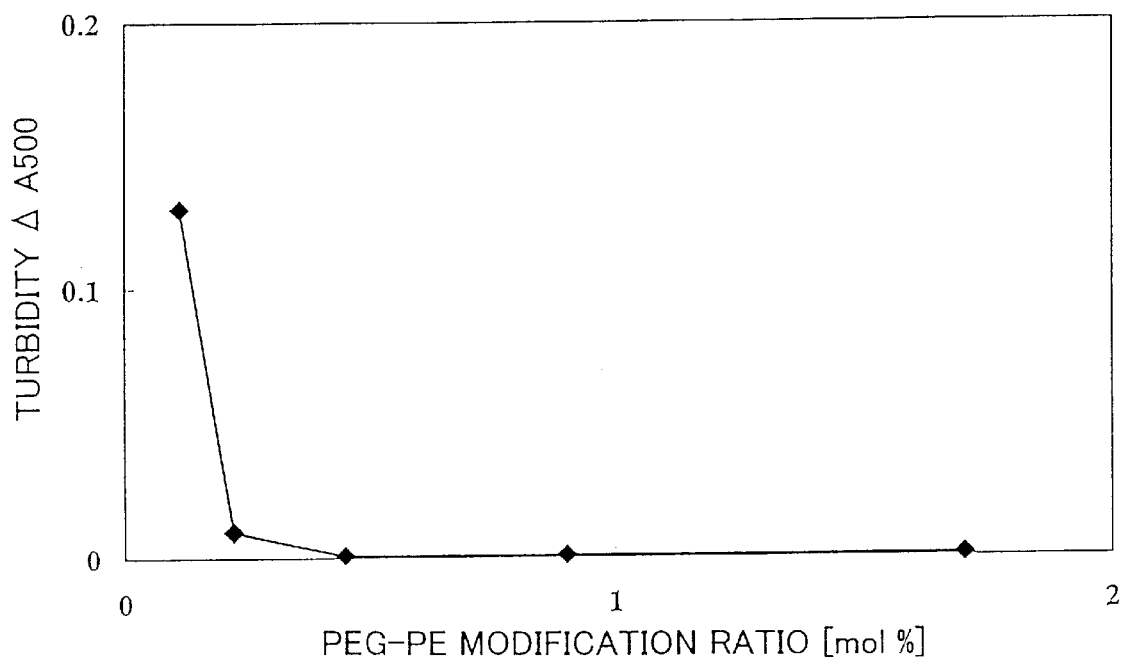
FIG. 9 is a graph showing a relationship between the modified amount of a hydrophilic polymer lipid derivative and the stability in serum in a liposome modified by a basic compound which takes positive charge within a physiological pH range.

The results are shown in FIG. 9.

When modified by various concentrations of the polyethylene glycol-phosphatidylethanolamine derivative, aggregation occurred at a low concentration modification range, and the modification range was 0.2 mol % or less.

That is, in order to prevent aggregation of liposomes in blood and ensure their stability, it is most desirable to set the modification ratio of hydrophilic polymer lipid derivative to 0.2 mol % or more.

Test Example 7

Examination of Accumulation on the Kidney (1)

The object of this testis to know influence of the surface modification by a basic compound which takes positive charge within a physiological pH range upon accumulation on proteoglycan producing tissues typified by the injured kidney.

\<Method\>

Anti-Thy-1 antibody nephritis rats were prepared by intravenously administering an anti-Thy-1 antibody solution through the caudal vein of each CD (SD) male rat. On the fifth day after administration of the anti-Thy-1 antibody, a Rhodamine-labeled liposome having a polyethylene glycol-phosphatidylethanolamine derivative modification ratio of 0.45 mol %, in which the liposome membrane was labeled with Rhodamine-PE, which had been prepared in accordance with the method of Preparation Example 1 or 7, was administered by intravenous injection to each rat at a dose of 500 µl through the caudal vein. The kidney was excised from each rat 24 hours thereafter. Unfixed frozen sections were prepared from the excised kidney, and the distribution of liposomes therein was observed under a fluorescence microscopy.

For the sake of comparison, distribution of liposomes in the kidney of normal CD (SD) male rat was observed by the same method.

\<Results\>

Figure 10:
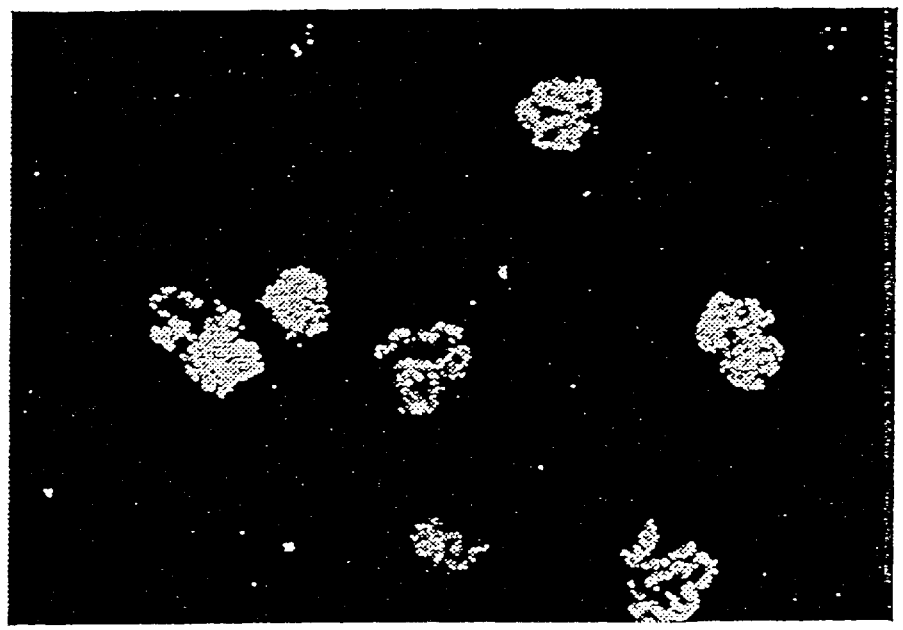
FIG. 10 is a schematic illustration showing accumulation of liposomes modified by a basic compound which takes positive charge within a physiological pH range on injured kidney.
Figure 11:
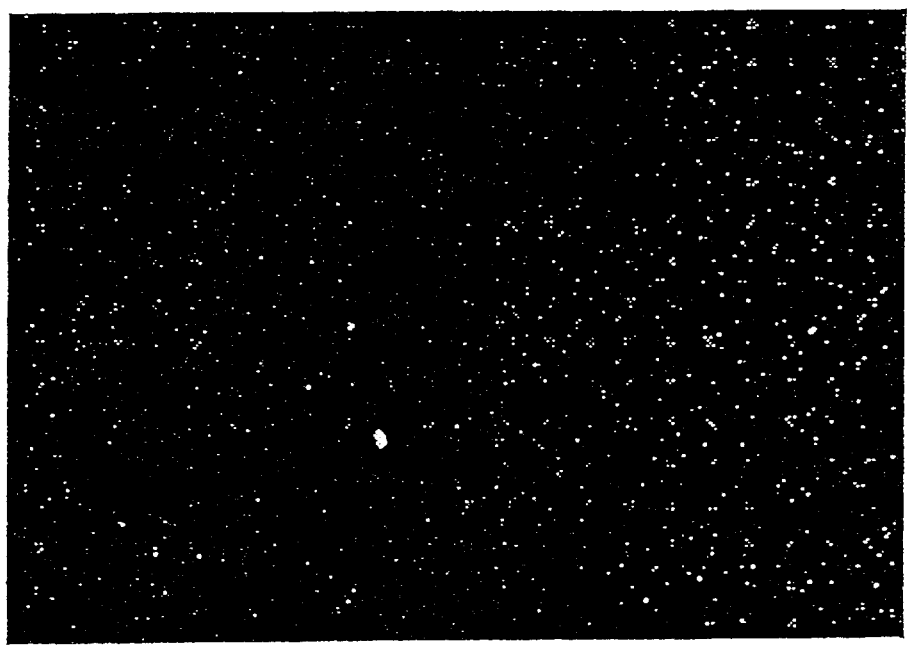
FIG. 11 is a schematic illustration showing that liposomes having neutral surfaces do not accumulate on injured kidney.

The results are shown in FIGS. 10 and 11. FIGS. 10 and 11 are schematic illustrations-prepared based on about 400× magnification fluorescence microphotographs. In FIGS. 10 and 11, liposomes of Preparation Examples 1 and 7 were used respectively.

When the liposomes prepared using an amidino group-containing compound (3,5-dipentadecyloxybenzamidine hydrochloride) as the basic compound which takes positive charge within a physiological pH range (Preparation Example 1) was compared with the liposomes prepared without using the compound (Preparation Example 7), it was confirmed that the former are accumulated specifically on the kidney which caused inflammation, particularly on the glomerulus. (In FIG. 10, white objects are Rhodamine-labeled liposomes.) Though not shown in the drawings, it was confirmed that the liposomes of Preparation Example 1 do not accumulate on the normal kidney.

That is, the liposomes whose surfaces are modified by a basic compound which takes positive charge within a physiological pH range have an excellent property to be accumulation on tissues and/or organs which excessively produce proteoglycan, typified by the injured kidney, particularly the glomerulus which was injured and thereby caused inflammation.

Test Example 8

Examination of Accumulation on the Kidney (2)

The object of this test is to know influence of the average particle size of liposomes upon their accumulation on proteoglycan producing tissues typified by the injured kidney.

\<Method\>

Anti-Thy-1 antibody nephritis rats were prepared by intravenously administering an anti-Thy-1 antibody solution through the caudal vein of each CD (SD) male rat. On the fifth day after administration of the anti-Thy-1 antibody, a Rhodamine-labeled liposome having a polyethylene glycol-phosphatidylethanolamine derivative modification ratio of 0.45 mol %, in which the liposome membrane was labeled with Rhodamine-PE, which had been prepared in accordance with the method of Preparation Example 1, 16 or 17, was administered by intravenous injection to each rat at a dose of 500 µl through the caudal vein. The kidney was excised from each rat 24 hours thereafter. Rhodamine-PE was extracted from the excised kidney and its fluorescence intensity was measured to calculate the distributed amount of liposomes in the kidney.

For the sake of comparison, distributed amount of liposomes in the kidney of normal CD (SD) male rat was observed by the same method.

\<Results\>

Figure 12:
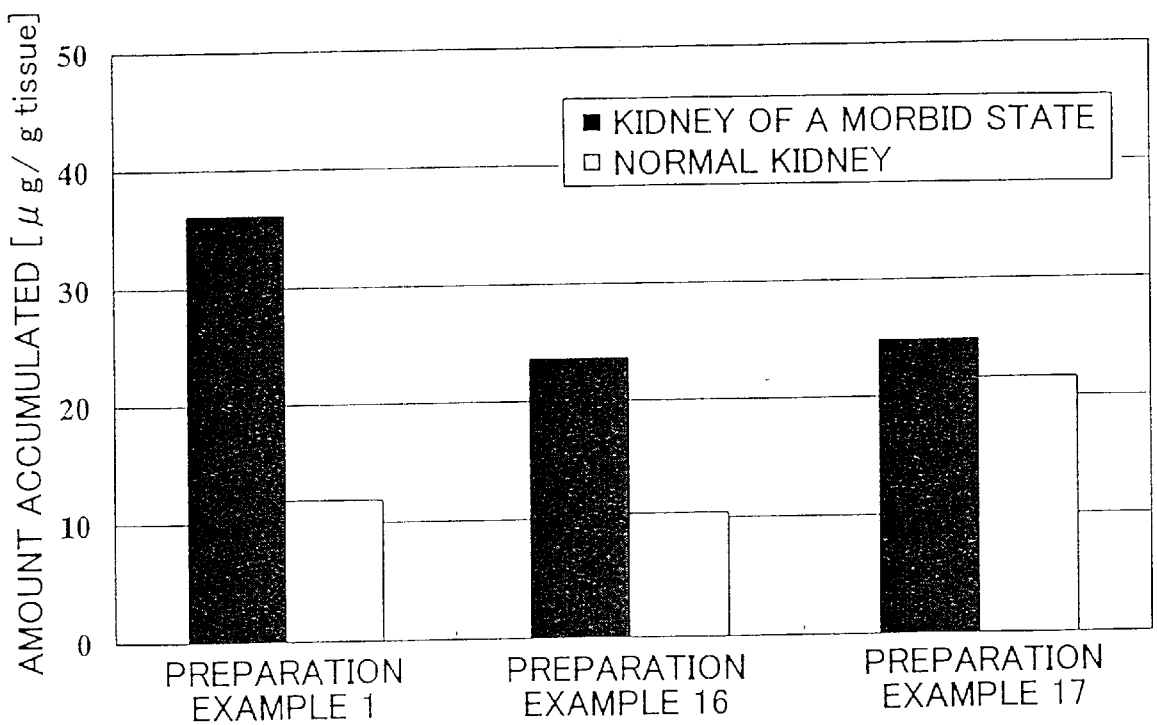
FIG. 12 is a graph showing a relationship between average particle size of liposomes and their accumulation on injured kidney.

The results are shown in FIG. 12.

It was confirmed that the liposomes having an average particle size of 122.2 nm and a major particle size range of from 90 to 200 nm (Preparation Example 1) have excellent property to accumulate on the kidney of a morbid state (injured kidney). It was confirmed also that, in the case of the liposomes having an average particle size of 273 nm and a major particle size range of from 180 to 350 nm (Preparation Example 16), their accumulated amount on the kidney of a morbid state is smaller than that of the case of Preparation Example 1, namely ⅔ or less, and their accumulated amount on the normal kidney is almost the same as the case of Preparation Example 1, and, in the case of the liposomes having an average particle size of 79.6 nm and a major particle size range of from 40 to 90 nm (Preparation Example 17), their accumulated amount on the kidney of a morbid state is smaller than that of the case of Preparation Example 1, namely about ⅔, and their accumulated amount on the normal kidney is about 2 times larger than the case of Preparation Example 1.

That is, in order to inhibit their accumulation on normal tissues and/or organs and to simultaneously effect their selective accumulation on proteoglycan overproducing tissues and/or organs typified by the kidney of a morbid state, it is most suitable to control the major particle size range and average particle size at a level of from 90 to 200 nm.

Test Example 9

Examination of Accumulation on the Kidney (3)

The object of this test is to know, in liposomes whose surfaces are modified by a basic compound which takes positive charge within a physiological pH range, influence of the kind of basic compound upon their accumulation on proteoglycan overproducing tissues and/or organs typified by the injured kidney.

<Method>

Anti-Thy-1 antibody nephritis rats were prepared by intravenously administering an anti-Thy-1 antibody solution through the caudal vein of each CD (SD) male rat. On the fifth day after administration of the anti-Thy-1 antibody, a Rhodamine-labeled liposome having a polyethylene glycol-phosphatidylethanolamine derivative modification ratio of 0.45 mol %, in which the liposome membrane was labeled with Rhodamine-PE, which had been prepared in accordance with the method of Preparation Examples 1, 2 or 3, was administered by intravenous injection to each rat at a dose of 500 μl through the caudal vein. The kidney was excised from each rat 24 hours thereafter. Rhodamine-PE was extracted from the excised kidney and its fluorescence intensity was measured to calculate the distributed amount of liposomes in the kidney.

For the sake of comparison, distributed amount of liposomes in the kidney of normal CD (SD) male rat was observed by the same method.

<Results>

Figure 13:
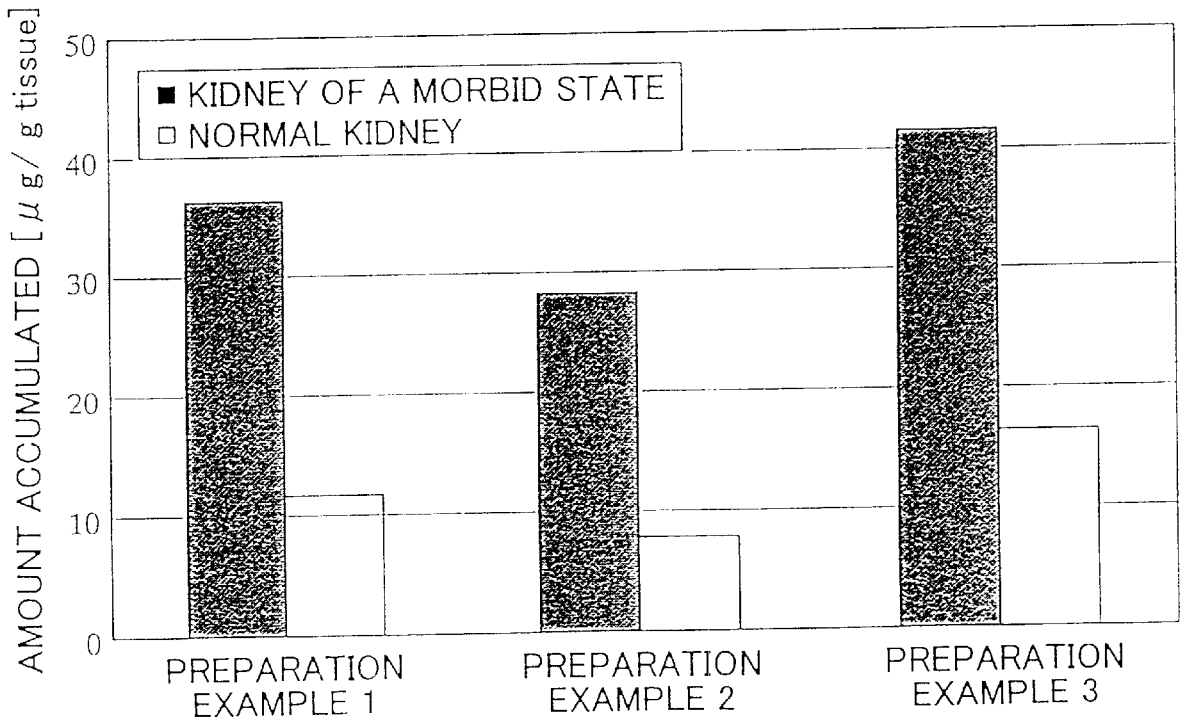
FIG. 13 is a graph showing a relationship between kinds of basic compound to be used in the surface modification of liposomes and their accumulation on injured kidney.

The results are shown in FIG. 13.

In the liposomes having any one of the basic compounds, their accumulation on the kidney of a morbid state was improved in comparison with the normal kidney, so that it was confirmed that modification of the surface by the basic compound which takes positive charge within a physiological pH range is important for positive targeting at the kidney of a morbid state. Also, the accumulation property varied depending on the kind of basic compound, and it was confirmed that particularly excellent accumulation property is obtained when 3,5-dipentadecyloxybenzamidine hydrochloride (Preparation Example 1) or N,N-dioctadecyl-2-(piperidin-4-yl-oxy)acetamide (Preparation Example 2) is used.

Test Example 10

Pharmacological Eeffect of the Liposomes of the Invention in which a Drug is Included The object of this test is know the degree of practical pharmacological effect exerted by the liposomes of the invention confirmed by the above Test Examples 1 to 9.

<Method>

Anti-Thy-1 antibody nephritis rats were prepared by intravenously administering an anti-Thy-1 antibody solution through the caudal vein of each CD (SD) male rat. On the fifth day after administration of the anti-Thy-1 antibody, the liposome dispersion liquid obtained in Preparation Example 15 (1 mg as prednisolone phosphate sodium) was administered by intravenous injection. On the tenth day after administration of the anti-Thy-1 antibody, urine was collected to measure the total protein content.

For the sake of comparison, the preparation of Comparative Example 1 (a liposome dispersion liquid having no included drug) or physiological saline was administered by the same method, and urine was collected on the tenth day after administration of the anti-Thy-1 antibody to measure the total protein content.

Also, a prednisolone phosphate sodium solution (1 mg as prednisolone phosphate sodium) which was not made into liposomes was administered once on the fifth day after administration of the anti-Thy-1 antibody, or five times (once a day for 5 days) started on the fifth day after administration of the anti-Thy-1 antibody, and urine was collected on the tenth day after administration of the anti-Thy-1 antibody to measure the total protein content.

Urine was also collected from un-treated normal rat to measure the total protein content.

<Results>

Figure 14:
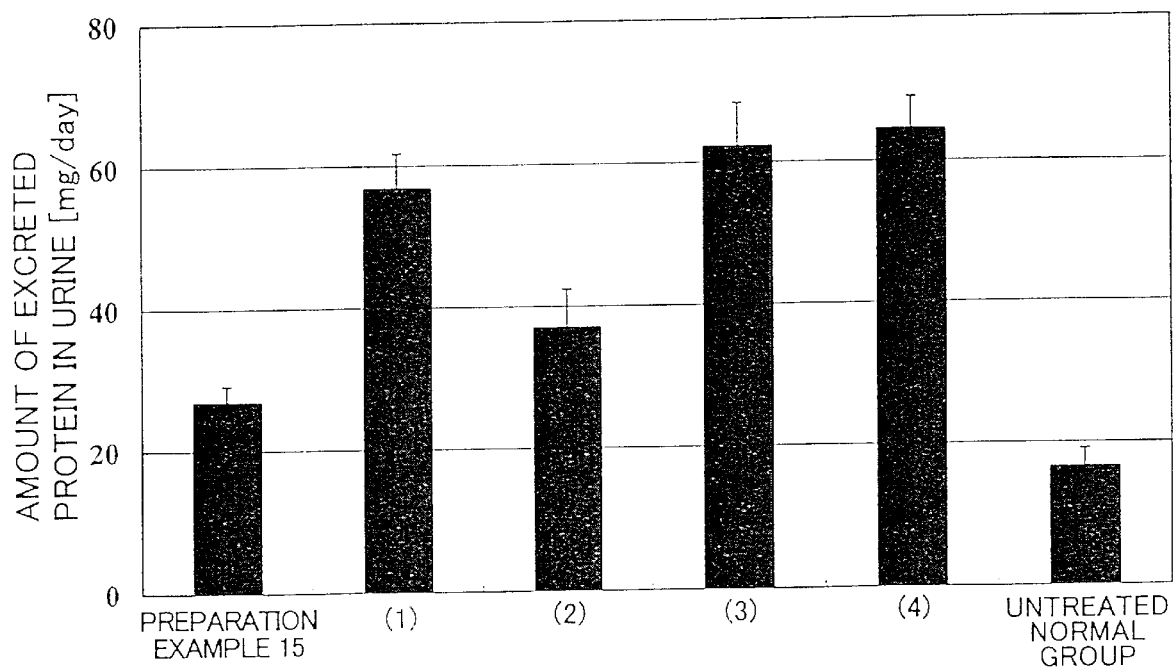
FIG. 14 is a graph showing pharmacological effects of the liposome of the invention.

The results are shown in FIG. 14.

Marks in FIG. 14 are (1): a group in which the prednisolone phosphate sodium.solution was administered once, (2): a group in which the prednisolone phosphate sodium solution was administered five times, (3): a group in which the liposome dispersion liquid containing no drug was administered once (Comparative Example 1) and (4): a group in which physiological saline was administered.

When the liposome of Preparation Example 15 as a liposome of the examples of the invention was administered, remarkable effect to inhibit excretion of protein into urine was found. This effect was even superior to a case in which prednisolone phosphate sodium equivalent to its amount included in the liposome of the invention was administered continuously for 5 days, namely five times larger amount as the total dose of prednisolone phosphate sodium, without making it into liposome.

Also, when the liposome with no drug included therein was administered or prednisolone phosphate sodium was administered once without making it into liposome in the same amount included in the liposome of the invention, the excreted amount of protein in urine was almost the same as the case of the administration of physiological saline, so that no effect was found.

That is, by only one administration, the liposome of the invention can exert a pharmacological effect similar to or larger than the case of a continuous administration of a drug which is not made into liposome. In consequence, it was confirmed that the use of the liposome of the invention renders possible insurance of the efficacy of a drug and reduction of the total dose of the drug.

Test Example 11

Acute Toxicity

The object of this test is to know the degree of toxicity of the liposome of the invention when compared with the toxicity of a conventional liposome. For this purpose, a liposome similar to the invention but having no drug included therein and a conventional liposome (also having no drug included therein) are respectively subjected to a rat lethal toxicity test.

<Preparation of Liquids to be Tested>

(1) A Liposome Dispersion Liquid of the Invention which Contains 3,5-Dipentadecyloxybenzamidine Hydrochloride and a Polyethylene Glycol-phosphatidylethanolamine Derivative The liposome dispersion liquid of the invention having a polyethylene glycol-phosphatidylethanolamine derivative modification ratio of 0.45 mol % obtained in Preparation Example 1 was used as a liquid to be tested, after its concentration using an ultrafiltration membrane and subsequent dilution with physiological saline as occasion demands.

(2) Conventional Liposome Dispersion Liquid

The liposome dispersion liquid of the invention having a polyethylene glycol-phosphatidylethanolamine derivative modification ratio of 0.45 mol % obtained in Preparation Example 7 was used as a liquid to be tested, after its concentration using an ultrafiltration membrane and subsequent dilution with physiological saline as occasion demands.

<Method>

Quarantined mice of five weeks of age were divided into groups of 5 animals per group, and each of the aforementioned liquid to be tested was administered through the caudal vein of each animal at a dose of 100 ml/kg. On the other hand, physiological saline was administered at a dose of 100 ml/kg in the solvent control group.

After administration of the liquid to be tested, general conditions were carefully observed at least once a day for 7 days, and toxicity signs and death cases were recorded. Also, pathologic autopsy was carried out after 7 days and each organ was excised. Pathologic sections were prepared from each organ and observed.

<Results>

Similar to the case of the conventional liposome (liposome dispersion liquid of (2)), no death case was found during the observation period in the liposome similar to that of the invention except that a drug was not included therein (liposome dispersion liquid of (1)). Also, no problematic pathological findings were obtained by the pathologic observation of each organ excised after 7 days.

That is, it was confirmed that the liposome of the invention has markedly low toxicity and high safety.

Industrial Applicability

Thus, as has been described in the foregoing, in comparison with the conventional liposomes, the liposome of the invention has high targeting ability for tissues and/or organs where proteoglycan is excessively produced typified by injured kidney, particularly the glomerulus which caused inflammation by injury, and also has high safety.

In consequence, the liposome of the invention is markedly effective for the purpose of diagnosing and treating diseases which accompany overproduction of proteoglycan in injured portions of tissues and/or organs, such as the case of glomerulonephritis.

What is claimed is:

1. A liposome in which a drug is included, which comprises
   (1) a basic compound selected from the group consisting 1,2-dipalmitoyl-3-trimethylammoniumpropane, 1,2-dipalmitoyl-3-dimethylamoniupropane, N',N"-dipentadecyltriethyltetramine, and the basic compounds represented by formulae 1 to 4;
   (2) a lipid derivative of a hydrophilic polymer; and
   (3) a lipid which constitutes the liposome, as its membrane constituting components, wherein their constituting ratios are from 1 to 20 mol % of (1) based on (3) and from 0.2 to 5 mol % of (2) based on the total of (1) and (3);

wherein said basic compounds represented by formulae 1 to 4 are represented by the following:

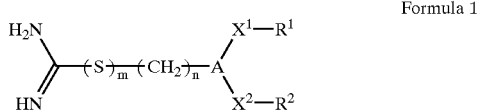

Formula 1 wherein A represents an aromatic ring, each of $R^1$ and $R^2$ represents an alyl or alkenyl group having from 10 to 25 carbon atoms, wherein $R^1$ and $R^2$ may be the same or different from each other, each of $X^1$ and $X^2$ represents —O—, —S—, —COO—, —OCO—, —CONH— or —NHCO—, wherein $X^1$ and $X^2$ may be the same or different from each other, m is 0 or 1 and n is 0 or an integer of from 1 to 6;

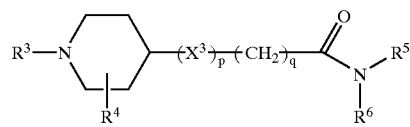

Formula 2 wherein $R^3$ represents hydrogen or an alkyl or alkenyl group having from 1 to 8 carbons atoms, $R^4$ represents hydrogen or an alkyl or alkenyl group having from 1 to 8 carbon atoms, each of $R^5$ and $R^6$ represents hydrogen or an alkyl or alkenyl group having from 1 to 25 carbon atoms (excluding a case in which $R^5$ and $R^6$ are both hydrogen), wherein $R^5$ and $R^6$ may be the same or different from each other, $X^3$ represents —O— or —S—, p is 0 or 1 and q is 0 or an integer of from 1 to 10;

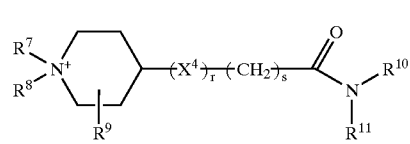

Formula 3 wherein each of $R^7$ and $R^8$ represents an alyl or alkenyl group having from 1 to 8 carbon atoms, wherein $R^7$ and $R^8$ may be the same or different from each other, $R^9$ represents hydrogen or an alkyl or alkenyl group having from 1 to 8 carbon atoms, each of $R^{10}$ and $R^{11}$ represents hydrogen or an alkyl or alkenyl group having from 1 to 25 carbon atoms (excluding a case in which $R^{10}$ and $R^{11}$ are both hydrogen), wherein $R^{10}$ and $R^{11}$ may be the same or different from each other, $X^4$ represents —O— or —S—, r is 0 to 1 and s is 0 or an integer of from 1 to 10); and

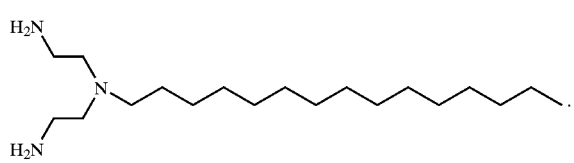

Formula 4

2. A method for the diagnosis and/or treatment of a disease that accompanies overproduction of chondroitin sulfate proteoglycan comprising administering to a mammal in need of such diagnosis and/or treatment a liposome having major particle size range of 90–200 nm obtained through a plural stage of filtration of different pore sizes by compression, in which a drug for the diagnosis and/or treatment of a disease that accompanies overproduction of chondroitin sulfate proteoglycan is included, which comprises (1) a basic compound which takes positive charge within a physiological pH range selected from the group consisting of an amidino group, two or more amino groups, a piperidine ring, a tertiary amino group and a quaternary amino group, (2) a lipid derivative of a hydrophilic polymer and (3) a lipid which constitutes the liposome, as its membrane constituting components, wherein their constituting ratios are from 5 to 15 mol % of (1) based on (3) and from 0.2 to 5 mol % of (2) based on the total of (1) and (3); and further wherein said liposome is the liposome according to claim 1.

3. The method according to claim 2, wherein the lipid derivative of a hydrophilic polymer is a lipid derivative of polyethylene glycol.

4. The method according to claim 3, wherein the aforementioned lipid derivative of polyethylene glycol is a compound which contains a polyethylene glycol chain and a diacyl glycerol in one molecule.

5. The method according to claim 3, wherein the lipid derivative of a hydrophilic polymer has a molecular weight of from 1,000 to 7,000.

6. A method for diagnosis and/or treatment of a disease that accompanies overproduction of chondroitin sulfate proteoglycan comprising administering to a mammal in need of such diagnosis and/or treatment a liposome according to claim 1 obtained through a plural stage of filtration of different pore sizes by compression, in which a drug for the diagnosis and/or treatment of a disease that accompanies overproduction of chondroitin sulfate proteoglycan is included.

7. The liposome according to claim 1, wherein said drug is an adrenocortical steroid and/or a derivative thereof.

8. The liposome according to claim 1, wherein said drug is a drug for diagnosing and/or treating a disease which accompanies overproduction of chondroitin sulfate proteoglycan in injured portions of tissues and/or organs.

9. The liposome according to claim 1, wherein the major particle size range of the aforementioned liposome is from 90 to 200 nm.

10. The liposome according to claim 1, wherein the lipid which constitutes the aforementioned liposome is a phospholipid or a hydrogenated product of a phospholipid.

11. The liposome according to claim 1, wherein it further contains a stabilizing agent or an antioxidant.

12. The liposome according to claim 1, wherein said membrane constituting component ratios are from 5 to 15 mol % of (1) based on (3) and from 0.2 to 5 mol % of (2) based on the total of (1) and (3).

13. The method according to claim 2, wherein said mammal is a human.

14. A method for diagnosis and/or treatment of a cell of overproduction of chondroitin sulfate proteoglycan comprising administering a mammal in need to a liposome having major particle size range of 90–200 nm obtained through a plural stage of filtration of different pore sizes by compression, in which a drug for the diagnosis and/or treatment of a cell of overproduction of chondroitin sulfate proteoglycan is included, which comprises (1) a basic compound which takes positive charge within a physiological pH range selected from the group consisting of an amidino group, two or more amino groups, a piperidine ring, a tertiary amino group and a quaternary amino group, (2) a lipid derivative of a hydrophilic polymer and (3) a lipid which constitutes the liposome, as its membrane constituting components, wherein their constituting ratios are from S to 15 mol % of (1) based on (3) and from 0.2 to 5 mol % of (2) based on the total of (1) and (3); and further wherein said liposome is the liposome according to claim 1.

* * * * *

UNITED STATES PATENT AND TRADEMARK OFFICE
CERTIFICATE OF CORRECTION

PATENT NO. : 6,562,371 B1  Page 1 of 1
DATED : May 13, 2003
INVENTOR(S) : Kazuo Kawahara et al.

It is certified that error appears in the above-identified patent and that said Letters Patent is hereby corrected as shown below:

<u>Title page,</u>
Item [75], Inventors, add: -- Hiroaki Kasukawa --.

<u>Column 14,</u>
Line 28, "Hpolyethylene" is replaced with -- polyethylene --.

<u>Column 17,</u>
Line 50, "trimethylarmoniwunpropane" is replaced with -- trimethylammoniumpropane --.

<u>Column 25,</u>
Line 51, "endbthelial" is replaced with -- endothelial --.

<u>Column 29,</u>
Line 37, "Eeffect" is replaced with -- Effect --.

<u>Column 31,</u>
Line 41, "dimethylamoniupropane" is replaced with -- dimethylammoniumpropane --.
Line 61, "alyl" is replaced with -- alkyl --.

<u>Column 32,</u>
Line 26, "alyl" is replaced with -- alkyl --.

<u>Column 34,</u>
Line 23, "S" is changed to -- 5 --.

Signed and Sealed this

Thirtieth Day of March, 2004

JON W. DUDAS
*Acting Director of the United States Patent and Trademark Office*